United States Patent [19]

Gibbons

[11] Patent Number: 4,807,163

[45] Date of Patent: Feb. 21, 1989

[54] METHOD AND APPARATUS FOR DIGITAL ANALYSIS OF MULTIPLE COMPONENT VISIBLE FIELDS

[76] Inventor: Robert D. Gibbons, 1560 N. Sandberg Terrace #307, Chicago, Ill. 60610

[21] Appl. No.: 760,666

[22] Filed: Jul. 30, 1985

[51] Int. Cl.[4] .................... G01N 15/00; G06K 9/46
[52] U.S. Cl. .................... 364/555; 364/550; 364/413.02; 382/18
[58] Field of Search .............. 364/550, 555, 558, 559, 364/413, 415; 33/512; 128/743; 356/440, 376–378; 382/5, 18, 62, 17

[56] References Cited

U.S. PATENT DOCUMENTS

| | | | |
|---|---|---|---|
| 3,521,235 | 7/1970 | Becker | 382/18 |
| 4,128,884 | 12/1978 | England | 364/555 |
| 4,151,512 | 4/1979 | Riganati et al. | 382/21 |
| 4,423,736 | 1/1984 | DeWitt et al. | 128/743 |
| 4,514,816 | 4/1985 | Ollus et al. | 364/555 |
| 4,563,096 | 1/1986 | Chidlow et al. | 356/440 |
| 4,581,762 | 4/1986 | Lapidus et al. | 364/559 |

Primary Examiner—Felix D. Gruber
Assistant Examiner—Brian M. Mattson
Attorney, Agent, or Firm—Neuman, Williams, Anderson & Olson

[57] ABSTRACT

A means and method for digitally analyzing multiple-component fields measures the relative proportional content of each component in the field. A selected field area is recorded to create a record which may be divided into a plurality of discrete segments each of which has an identifiable intensity, such as an ascertainable visible intensity. The visible intensity of each discrete segment is digitally resolved into one of a preselected multiple of discrete gray-level values, the frequency of which may then be registered to obtain a frequency distribution, such as a histogram. The frequency distribution is resolved, such as through a Gaussian mixture analysis, to approximate the observed data by multiple, normally distributed component distributions. Each of the component distributions is then representative of a selected component of the field, thereby providing a measure of the proportional content of the field area which is comprised by each component. Additional embodiments simplify the analysis of the multiple-component field by initially identifying a visible intensity typically associated with each component and subsequently analyzing the frequency of occurrence of that particular visible intensity among the digitally resolved field segments.

15 Claims, 5 Drawing Sheets

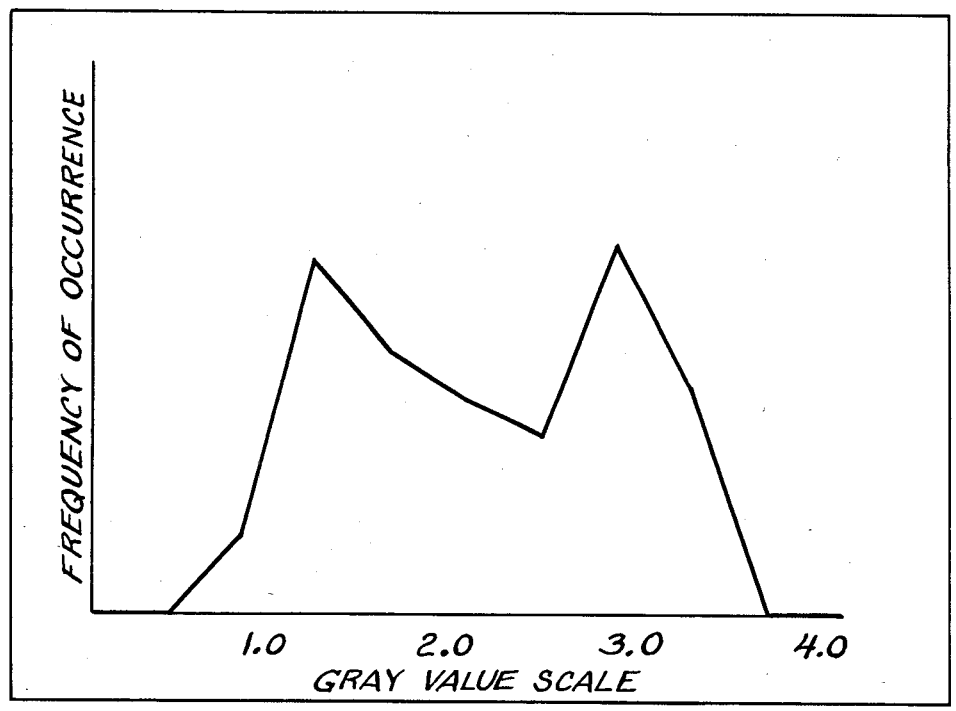
FIG. 5
FIG. 6
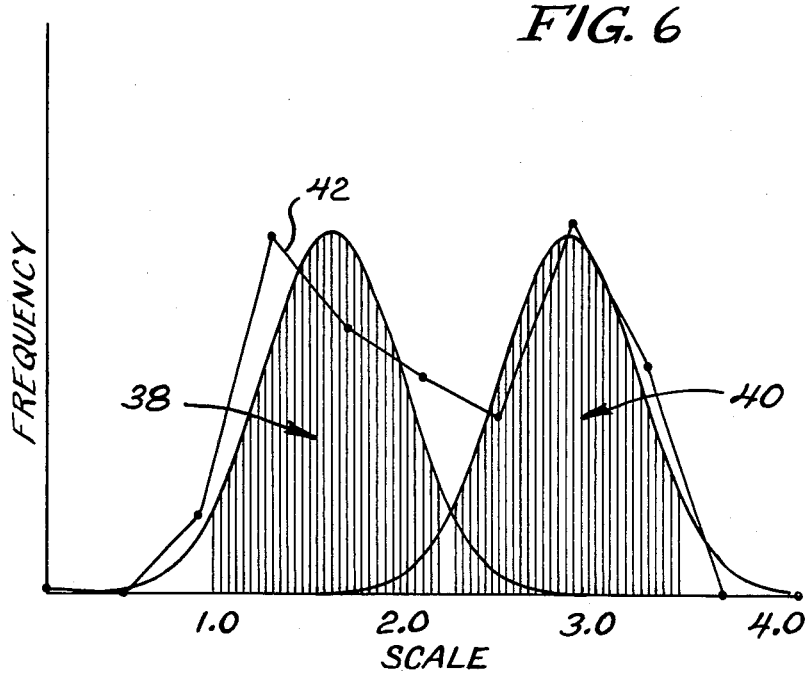

METHOD AND APPARATUS FOR DIGITAL ANALYSIS OF MULTIPLE COMPONENT VISIBLE FIELDS

BACKGROUND OF THE INVENTION

The present invention generally relates to the field of multiple-component field analysis. More particularly, the present invention pertains to digital determination of the relative proportional content of individual components in multiple-component fields.

Generally, the desirability of being able to immediately assess the relative content comprised of any particular component in a defined area of two or more distinct components has gone unrecognized. For example, it may be desirable to quickly and accurately determine the percentage of farm acreage flooded during spring rains, the proportion of trees in a forest that have been damaged by forest fire or by drought, or the percentage of a human head which is covered by hair. Frequently, visual estimates may provide the sole basis for such data. However, accurately monitoring the percentage of the human scalp covered by hair can provide a ready indication of the amount of new hair growth. This is of particular interest in monitoring the beneficial results of individual hair growth treatments for male pattern baldness, diffuse alopecia areata, or other hair related disorders.

For years concern has existed over the predominance and uncontrollability of male pattern baldness. Many and various solutions and treatments have been proffered to the public for overcoming this condition, including assorted tonics and hair transplants. Because of the relative lack of success of the vast majority of these treatments, the Food and Drug Administration (F.D.A.) has been extremely reluctant to grant approval for any medical product designed to rejuvenate the growth of hair on the scalp or other body regions. In the face of substantial opportunities for fraud, the F.D.A. requires extensive, detailed analysis and substantiation for any claims of renewed hair growth. Accordingly, many drug manufacturers have gone to great lengths to provide such substantiation.

Hair growth has been traditionally monitored by initially counting each hair on a specified scalp area prior to application of a hair growth formula. Subsequently, after a predetermined observation period, each and every hair in the specified scalp region is again counted. In this fashion, the number of additional hairs sprouted during the observation period may be determined and the degree of success of the treatment monitored.

However, this method may be extremely time consuming and expensive. Furthermore, this method suffers serious drawbacks in its accuracy and reliability. Accordingly, it is desirable to provide a method and apparatus for readily and accurately analyzing a scalp region to determine the increase in hair growth which occurs during the observation period in response to the hair growth treatment.

Similar problems may also occur in related medicinal applications. For example, it may be desirable to monitor the decrease of acne in the facial region in response to treatment by acne medicine. Likewise, it may be desirable to monitor the decrease of scar tissue or the degree of healing indicated by such a decrease in scar tissue. Similarly, in health safety studies conducted with animals, it may be desirable to assess the degrees and extent of skin irritation, erythemia, produced by topical application of a putative industrial irritant. Accordingly, it is desirable to provide a method and apparatus which may readily provide an accurate and reliable measure of the percentage of a defined area which is covered by scar tissue or other surface abnormalities such as acne.

Outside the field of medicine, the same type of difficulties frequently occur. Although the proportional content of one or more components in a particular area may be the most telling evidence of particular pheonomena, such evidence may not be readily obtainable. Factors such as cost, accuracy and reliability may render unsatisfactory most currently utilized products and methods, including physical counts and visual approximations. Accordingly, it is desirable to provide a means and method for digitally analyzing the proportional content of each component in multiple-component fields.

Therefore, it is a principal object of the present invention to provide a method and apparatus of digital field analysis for generally overcoming the deficiencies of the prior art.

It is a further object of the present invention to provide a method and apparatus for digitally analyzing multiple-component visible fields.

It is still a further object of the present invention to provide a method and apparatus to allow accurate and reliable measurement of the percentage of change in proportional content for one or more components in a multiple-component field over a particular observation period.

It is a related, particular object of the present invention to provide a method and apparatus for digitally measuring the percentage of a human scalp region which is comprised of hair. It is a corresponding further object of the present invention to provide a method and apparatus which allows an accurate and reliable measurement of the percentage change in the proportional area of the scalp region covered by human hair in response to treatment over a specified observation period.

SUMMARY OF THE INVENTION

The present invention generally provides a method and apparatus for digitally analyzing multiple-component fields to quantify the relative proportional content attributable to each component. A visible field is recorded to create a preferably fixed record divisible into a plurality of discrete segments. Each segment will then have an identifiable intensity. Subsequently, the intensity of each segment will be digitially resolved into one of a multiple of discrete values. For example, one of two-hundred fifty-six (256) shades of gray. The frequency of occurrence of each discrete value may then be registered to obtain a frequency distribution. That distribution is resolved, through a Gaussian mixture analysis for example, into multiple, normally distributed component distributions, each being representative of a selected component, thus providing a measure of the proportional content of the visible field comprised by each component.

To obtain the percentage change in the proportional content of each component in response to a selected treatment, the above outlined process is repeated after a predetermined observation period. Accordingly, the percent change in the proportional content of each component will be precisely representative of the corresponding increase or decrease of that component in the selected field.

Also, the apparatus and methodology of the present invention may be utilized in further embodiments to digitally analyze a multiple-compponent field to determine the relative proportional content of each component. In one such technique, a first section of the field area in which only one component is present is first recorded. The intensity of the component present in that first segment is then digitally resolved into an identifiable, discrete value. Subsequently, each separate component in the field is similarly identified and a digital value assigned to the respective intensity of each component by recording discrete sections of the field area comprised entirely of the respective component. The entire selected field area is then recorded to create a field record divisible into a plurality of discrete segments, for which the intensity level may be digitally resolved into a discrete value. By comparing the discrete value for each segment with the discrete values identified for each of the components of the field, the discrete values may be organized into identifiable groups by determining whether the discrete value for a particular segment falls within a predetermined range about an identified value for a particular component of the field. The relative proportional content of each component then may be determined by the frequency of occurrence of that component's measured intensity level among the total number of field segments.

The method and apparatus of the present invention may be particularly applied to analysis of human scalp regions to monitor any increase or decrease in the proportional content of hair or scalp in a particular head region.

A further embodiment of the means and method of the present invention may be utilized to digitally analyze a two component optical field to determine the relative proportional content of each component. A particular measured gray level is intially identified for each of the components. The entire optical field is then scanned, divided into discrete segments, each segment assigned a digital gray level and each segment identified as either a first or second component based upon whether its gray level value has a greater probability of being in the first or second component. Accordingly, a representative optical field may be divided into two component portions and the relative proportional content of each measured.

BRIEF DESCRIPTION OF THE FIGURES

Those features of the present invention which are deemed to be novel are set forth with particularity in the appended claims. The invention, together with the objects and advantages thereof, may be best understood by reference to the following detailed description taken in conjunction with the accompanying drawings in which like elements are identified by like reference numerals, and of which:

FIG. 5 is an illustration of a histogram generated in accordance with the present invention and illustrating discrete intensity levels of the digitized display;

FIG. 6 is a graphic representation of a two component, mixed Gaussian function which is superimposed over the histogram of FIG. 5 to illustrate an approximate fit of the statistical representation in accordance with the means and method of the present invention;

DETAILED DESCRIPTION OF THE INVENTION

The invention will be described below in connection with several preferred embodiments and procedures. However, the invention is not intended to be limited to the particular embodiments and procedures described. On the contrary, all alternatives, modifications and equivalents as would be apparent to one of ordinary skill in the art and familiar with the teachings of this application should be deemed to fall within the spirit and scope of the present invention, as defined by the appended claims.

In accordance with the present invention, a representative field comprised of multiple-components may be digitally analyzed to determine the relative proportional content of each component. For illustrative purposes only, the present invention may be discussed in terms of a particular application, that is, the monitoring of the density of hair on the human scalp as would typically be done to quantitatively measure the efficacy of various hair growth treatments.

Figure 1:
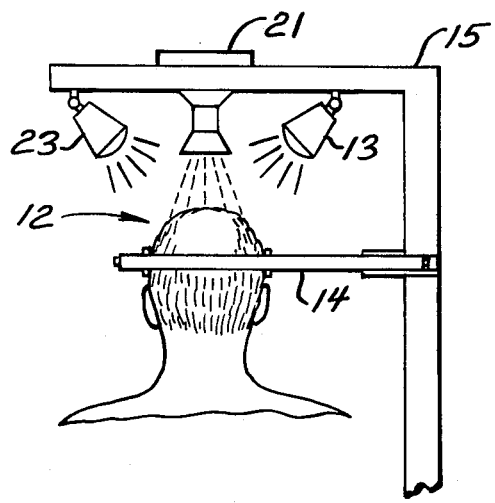
FIG. 1 is a view of one embodiment for utilizing the means and method of the present invention for analyzing a multiple-component field such as a human scalp region.

Referring now to FIG. 1, therein is shown an arrangement for facilitating the practice of the present invention in monitoring hair density. More particularly, a selected head region 12 is recorded by a video camera 21, or other suitable photographic device. Lights 13 and 23 serve to facilitate photographing the head region 12 by providing necessary lighting. Further, a head restraining device 14 mounted on a frame 15 provides a steady rest so that the head region 12 may be held stably in place during photographing. Also, a device 14, which may include a chin rest, serves to provide a standard setting so that the head region 12 may be fixedly photographed on multiple occasions over a period of time while providing an identical field area to the camera 21.

Figure 2:
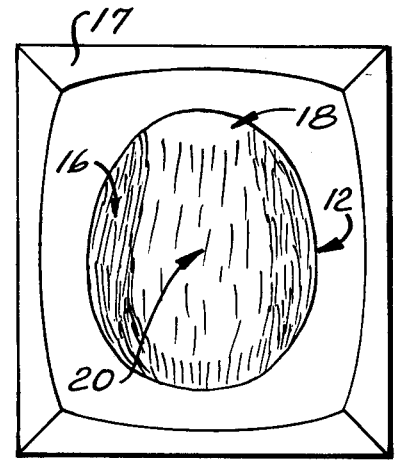
FIG. 2 is a representation of an initial visual display of a scalp area which is to be analyzed in accordance with one embodiment of the present invention.

Referring now to FIG. 2, therein is shown a visual representation of an image of the head area 12 produced by the camera 21. In the preferred embodiment illustrated in FIGS. 1 and 2, the camera 21 represents a video camera which may be connected directly to a video display device 17. Accordingly, the head region 12 may be displayed on a video monitor for accurate positioning within a frame 19 in cooperation with the restraining device 14 prior to further processing. Alternatively, a still photograph may be taken of the selected scalp region and the photograph used for subsequent analysis. When this procedure is followed, head region 2 is permanently recorded on film, and then the photograph is analyzed digitally as explained below.

As illustrated in FIG. 2, the head region 12 comprises an area 16 which is largely hair and an area 18 which is composed virtually entirely of human scalp. Additionally, the head region 12 contains a large area 20 composed of a mixture of scalp and hair. In the practice of the present invention in accordance with a preferred embodiment for measuring hair density, it is desired to determine the proportional content of hair and the proportional content of scalp. By measuring the change in the proportional content comprised of hair over a predetermined observation period, such as thirty-six (36) weeks, hair growth may be readily monitored and quantified as a percentage increase or decrease.

The visual record as illustrated in FIG. 2 may be further processed in accordance with the present invention to determine the relative densities of each visual component. For example, in the embodiment shown in FIG. 3, the camera 21 is connected directly to a digitizer 22 by means of an appropriate bus connection 24. The digitizer 22 divides the analog picture display of FIG. 2 into a multiplicity of discrete segments each having a discrete, digital gray value. The gray values for each of the identified discrete segments of the visible field are then transmitted via a suitable bus 26 to an appropriate frame storage device 28.

In the illustrated embodiment of the present invention, the camera 21 is a video camera from which the analog output is directly connected to the digitizer 22. The illustrated display of FIG. 2 comprises a single frame, which is a typical video display is transmitted every one-thirtieth (1/30) of a second. The digitizer 22 divides the video frame into a digital representation having, for example, 500 vertical and 500 horizontal screen locations, otherwise known as pixels. Each of these pixels is described by a discrete gray level, which is digitally identified as an 8-bit binary word. Use of an 8-bit binary word provides two-hundred fifty-six (256) possible shades of gray for each of the approximately 250,000 pixels. These values may then be stored in an 8×256K memory device, such as the frame storage 28.

Figure 4:
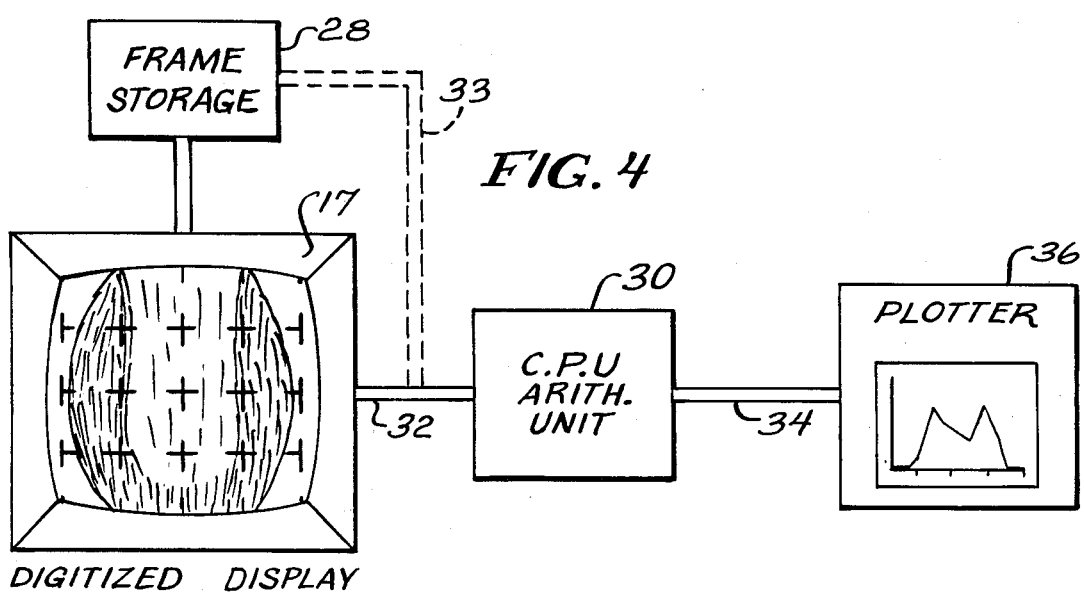
FIG. 4 is a further schematic representation of a digitized display of the initial visual display of FIG. 2, illustrating the discrete segments thereof and further processing means for facilitating the practice of the present invention.

The video image stored by the frame storage means 28 may then be redisplayed on a video display monitor 17 such as illustrated in FIG. 4 as a digitized display. FIG. 4 also illustrates a CPU arithmetic unit 30 which is used to further process the digital information stored in the frame storage 28. A suitable bus 32 connects the CPU unit 30 and the video monitor 17. Also, as illustrated by dashed line 33, the CPU arithmetic unit 30 may be directly connected to the frame storage unit 28, as the digitized video information need not be displayed on the video monitor to practice the present invention. The CPU arithmetic unit 30 is further connected by a bus 34 to a suitable plotter device 36 to provide a plot of the output of the CPU arithmetic unit 30.

In accordance with the present invention, the digital video information stored in the frame storage means 28 is representative of the visual field illustrated by the human head area 12 as shown in FIG. 2. As mentioned above, in the frame storage 28 the human head area 12 comprises approximately 250,000 separate gray-level words in a digital format. The CPU arithmetic unit 30 processes this digital information to register the frequency of occurrence of each discrete gray value in the total 250,000 pixels stored in the frame storage 28. The CPU unit 30 then provides the information to the plotter 36 to generate an illustrative plot as desired.

It is envisioned that the CPU unit 30 may comprise any suitable digital processing means. For example, an IBM AT personal computer or other similar personal computer may be readily utilized.

An illustrative plot produced by the plotter 36 from the processing of the gray-level values of the visible field pixels by CPU unit 30 is illustrated in FIG. 5. The plot of FIG. 5 may be conveniently referred to as a frequency histogram or a frequency distribution and provides a ready indication of the occurrence frequency of each discrete gray value in the total number of pixels comprising the visible field to be studied. As illustrated in FIG. 5, the gray value is represented along a horizontal scale and the frequency of occurrence of any particular gray value along the vertical axis. Thus, in accordance with the practice of the means and method of the present invention, a visual field, such as defined by the human head area 12, may be recorded, digitized and ultimately displayed as a frequency histogram of discrete gray levels.

For digitally recording an analog visual signal such as illustrated in FIG. 2, any suitable method and apparatus may be employed. For example, the various algorithms and image analysis for computer graphics set forth in Pavlides T., *Algorithms for Graphics and Image Processing*, Computer Science Press, Rockville, 1982, may be utilized to create the digitally stored frame image of the visual analog image of FIG. 2. Additionally, any suitable real time video digitizer module for use with personal computers may be utilized, such as currently available from Imaging Technology Incorporated, 600 West Cummings Park, Walburn, Mass. 01801, and described in a publication entitled "PC Vision, Frame Grabber". Accordingly, the video monitor 17 illustrated in FIG. 4 may be replaced with a personal computer display for providing a video output display of the digitized information contained in the frame storage 28.

Referring once again to FIG. 5, the frequency histogram illustrated therein comprises a representation of the gray levels which may be typically obtained from an analysis of a head region 12, such as illustrated in FIG. 2, comprising areas of predominantly hair, predominantly scalp and a mixture of the two. As shown in FIG. 5, such a frequency histogram desirably contains two identifiable peaks. For the particular field corresponding to the data of FIG. 5, the first peak occurs at approximately 1.5 on the horizontal axis as illustrated. The second such peak occurs at approximately 3.0 on the horizontal axis as illustrated.

In accordance with the practice of the present invention, the histogram of FIG. 5 may be resolved into a two-component Gaussian mixture distribution such as is illustrated in FIG. 6. A single Gaussian distribution may be represented by the following formula:

$$f(x) = \frac{1}{s\sqrt{2\pi}} e^{(xi-u)2/2s2} \quad (1)$$

where
u is the mean of the distribution, and
s is the standard deviation.

A two-component mixed Gaussian distribution as shown in FIG. 6 may be represented by the following formula:

$$f(x) = p\frac{1}{s_1\sqrt{2\pi}} e^{(xi-u1)2/2s12} + (1-p)\frac{1}{s_2\sqrt{2\pi}} e^{(xi-u2)2/2s22} \quad (2)$$

where,
$x_i$ is the observed gray scale value for screen location (pixel) i;
$u_1$ is the mean of the first component distribution;
$u_2$ is the mean of the second component distribution;
$s_1$ is the standard deviation of the first component distribution;
$s_2$ is the standard deviation of the second component distribution; and
p is the proportion of the image in pixels (i.e., screen location) having gray-scale values corresponding to the first component distribution; and correspondingly $(1-p)$ is the proportion of the image in pixels having gray-scale values corresponding to the second component distribution.

Referring again to FIG. 6, the first-component distribution 38 has a mean gray-scale value of approximately 1.5. Similarly, the second component distribution 40 has a mean value of approximately 3.0 on the gray-scale axis. The two component Gaussian distributions approximately match or "fit" the identified peaks in the frequency histogram illustrated by a trace 40 in FIG. 6 and shown clearly in FIG. 5. Either of the Gaussian component distributions 38 and 40 may be generally given by equation (1) above with the appropriate values substituted.

On the gray-scale (horizontal) axis, the lighter shades of gray will have a gray-scale value greater than darker shades. Accordingly, the second component distribution 40 which corresponds to the second peak in the frequency histogram trace 42 represents predominantly scalp areas (e.g., area 18) in the head region 12 as illustrated in FIG. 2. Correspondingly, the first component distribution 38 which matches the first peak in the frequency histogram trace 42 corresponds to the predominantly hair-covered areas (e.g., area 16) of the head region 12. Accordingly, the proportion, p, of the total number of screen pixels which may be found in the first component distribution 38 is representative of the proportion of the head region 12 which is covered by hair. Accordingly, hair density may be measured as that proportion of pixels having a gray-scale value falling within the first component distribution 38.

Although described immediately above in terms of a two-component visible field such as would be typically represented by the human head area as shown in FIG. 2, the present invention may be utilized to determine the proportional content of each component of any multiple-component field. For utilization with more than two-component distributions, equation (2) above would be generalized as follows:

$$f(x) = \sum_{j=1}^{M} p_j \left( \frac{1}{s_j\sqrt{2\pi}} e^{(xi-uj)2/2sj2} \right) \quad (3)$$

or, $$f(x) = \sum_{j=1}^{M} p_j \Phi(x_i) \quad (4)$$

where
$u_j$ is the mean of component distribution j;
$p_j$ is the proportion of the image comprised by component j; and
M is the number of component distributions where:

$$p_M = 1 - \sum_{j=1}^{M-1} p_j \quad (5)$$

Figure 3:
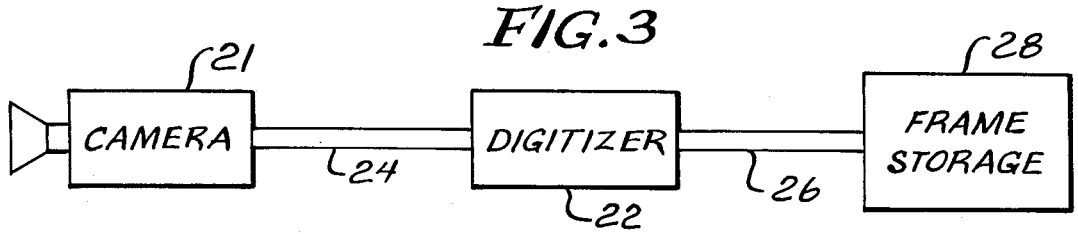
FIG. 3 is a schematic representation of one embodiment of the present invention for creating a digital record of a visible field record such as is illustrated in FIG. 2.
Figures 7, 8, 9:
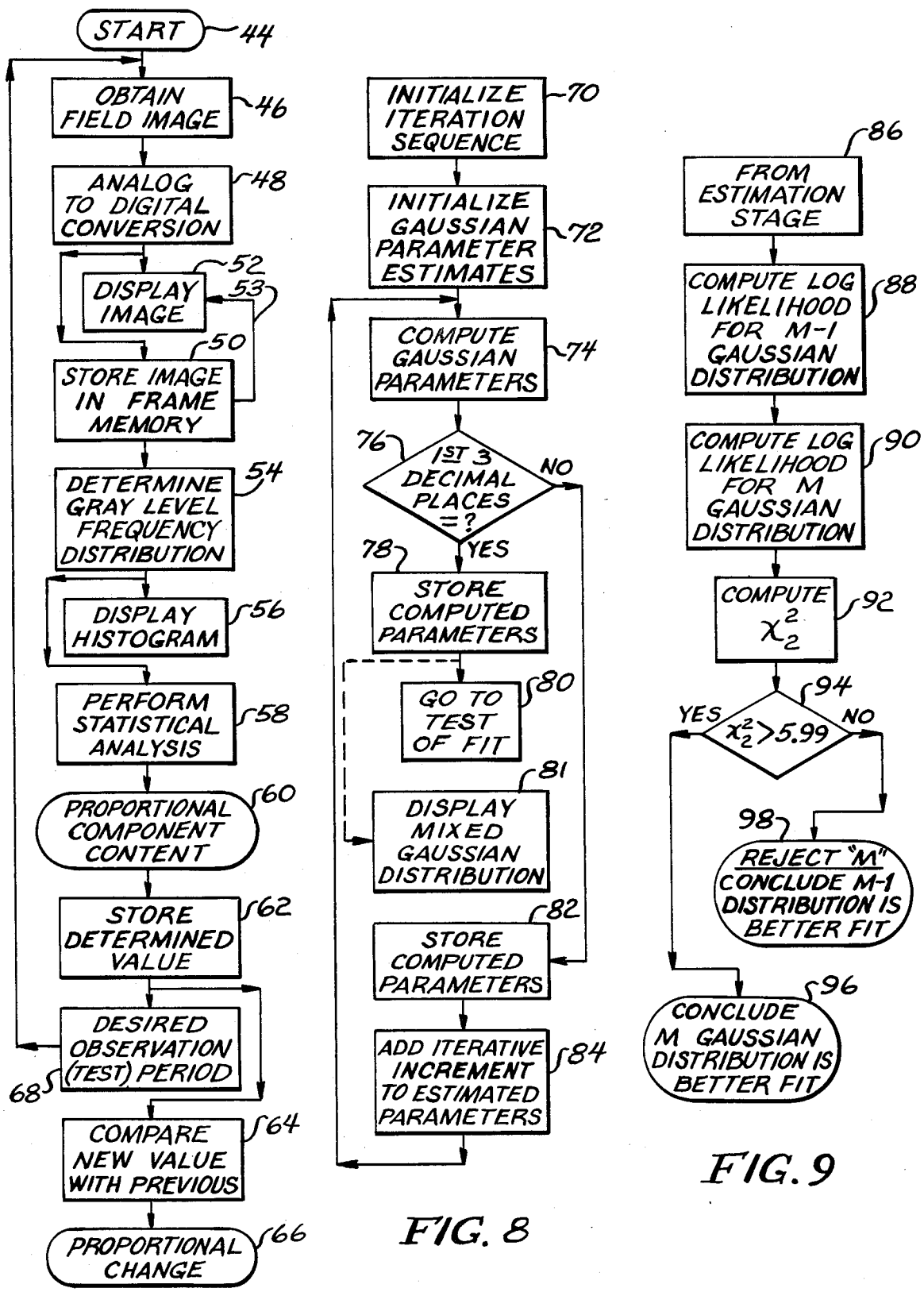
FIG. 7 is a schematic flowchart representation of a preferred embodiment of the method of the present invention.
FIG. 8 is a schematic flowchart representation of a selected embodiment of statistical Gaussian mixture analysis for a preferred embodiment of the present invention to approximate the Gaussian distributions for the actual data determined in the digitization phase.
FIG. 9 is a schematic flowchart representation of a selected embodiment of statistical analysis for determining the statistical fit between the actual data and the mixed Gaussian function in accordance with a preferred embodiment of the present invention.

Referring now to FIG. 7, therein is shown a general flowchart which outlines the procedures for the operation of the means and method of the present invention for obtaining the proportional content of each component in a multiple-component field. Specifically, as illustrated by a block 44 the method is initiated as shown in FIG. 1 by positioning and aligning the selected field to be analyzed. A record of the field image is then obtained, as shown by a block 46, by suitable means such as the video camera 21 or another photographic/video device. The obtained field image is then digitized as represented by block 48 through the use of digitizing equipment such as that shown by the digitizer 22 in FIG. 3. The digitized information representative of the intial field image is then stored as shown by a block 50 in a frame storage 28 such as is shown in FIG. 3. The digitized information may be displayed prior to storage as shown by block 52. Alternatively, if desired, the digitized display may be reproduced directly from the frame memory as shown by line 53. Block 54 represents the arithmetical analysis of the digitized information stored in the memory to determine the gray level frequency distribution. This may be done, for example, by the CPU arithmetic unit 30 illustrated in FIG. 4. The resulting frequency distribution of the stored gray levels may then be displayed as a histogram as shown by block 56 which corresponds to the use of the plotter 36 of FIG. 4 to obtain a plot such as is shown in FIG. 5.

Once the frequency distribution of the stored pixel gray levels comprising the selected field has been determined, a statistical analysis as illustrated by block 58 is performed to provide a measure of the proportional content of each component. This statistical analysis is described in greater detail in conjunction with the flowchart of FIG. 8. The result is the proportional content of each component as illustrated by block 60. This provides an accurate measure of each component content in the selected field at the time of the initial field recordation.

Once the proportional content of each component of the selected field has been determined, this value may be stored for later evaluation as shown by block 62. If the operation has been previously performed on this selected field, the new value for the proportional content of each component may be compared with the previous value as illustrated by block 64. The result then will be the change in proportional value for each component in the field. For example, the net increase or decrease in percentage of the head region 12 comprised of hair may be accurately determined. However, if the analysis has not previously been performed for this particular selected field, a desired observational test period is allowed to elapse as represented by block 68. After the termination of the observation period, a second image of the same field is obtained as illustrated by block 46 and the process repeated so that a comparison may be made between the proportional content for each component in the selected field prior to and subsequent to the desired observation period.

Referring now to FIG. 8, therein is shown a general flowchart for a preferred embodiment of the statistical analysis which may be used for the estimation phase for resolving the frequency distribution of the gray levels in the stored digitized video frame into multiple-component mixed Gaussian distributions. Specifically, in a preferred embodiment of the means and method of the present invention, the iteration sequence is initialized as represented by block 70. Once the iteration sequence has been initialized, the Gaussian parameter estimates are correspondingly initialized as indicated by block 72. Utilizing the estimated Gaussian parameters provided by the initial estimates from block 72, a computation as shown by block 74 is performed to compute intermediate Gaussian parameters corresponding to the anticipated component Gaussian distribution. As shown by decision block 76 in the preferred embodiment, the computed values are then compared with the estimated values to determine whether the first three decimal places are equal for each parameter. If yes, then the computer parameters are stored as shown by block 78 and the statistical analysis progresses to a test of fit determination as shown by block 80 which is described in more detail in conjunction with the corresponding flowchart of FIG. 9.

However, if the first three decimal places of the computed Gaussian parameters are not equivalent to the corresponding values in the estimated Gaussian parameters, then the computed parameters are stored as shown by block 82. Subsequently, an increment is added to the estimated parameters in accordance with a selected iterative sequence as shown by block 84. The analysis then loops back to block 74 at which time intermediate Gaussian parameters are again computed utilizing the incremented estimated parameters. The remaining steps are then repeated until the first three decimal places for each Gaussian parameter remain constant between two successive iterations. At that time the values are stored and test of fit analysis is performed.

Also, at this point the mixed Gaussian distribution may be displayed as shown by block 81. Such a display in conjunction with a gray-level histogram is illustrated in FIG. 6.

Block 74 of FIG. 8 represents the computation of the Gaussian parameters utilizing the initial estimates. This computation may be given by the following formulas:

$$p_j = \frac{1}{n} \sum_{i=1}^{n} Z(j/x_i) \quad j = 1, 2, \ldots, M-1 \quad (6)$$

$$u_j = \frac{1}{np_j} \sum_{i=1}^{n} Z(j/x_i) x_i \quad j = 1, 2, \ldots, M-1 \quad (7)$$

and,

-continued $$s_j = \frac{1}{np_j} \sum_{i=1}^{n} Z(j/x_i)(x_i - u_j)(x_i - u_j) \quad (8)$$

Where:

$$Z(j/x_i) = \frac{\Phi(x_i)}{p_j f(x_i)} \quad (9)$$

and n is the total number of screen locations.

Although a preferred embodiment for estimating the desired Gaussian parameters is set forth in conjunction with the accompanying computer program, general methodology for performing the desired Gaussian mixture analysis is set forth with some particularity in Day, N. E., "Estimating The Components Of A Mixture Of Normal Distributions," *Biometrika*, 56: 463-474, 1969.

Referring now to FIG. 9, therein is shown a general flowchart for determining whether the fit between the measured data represented by the gray levels of the pixels of the digitized field is adequately represented by the statistically determined M component Gaussian distribution. Block 86 represents a transition from the estimation phase in which the Gaussian parameters are determined to the test of fit stage illustrated further in FIG. 9. Initially, the log likelihood for an $M-1$ component Gaussian distribution is computed as shown by block 88. For a two-component Gaussian distribution, this likelihood is given by the following equation:

$$L_1 = \sum_{i=1}^{n} \log(f_1(x)) \quad (10)$$

where $f_1(x)$ is given by equation (1).

After the log likelihood for an $M-1$ component mixed Gaussian distribution has been determined, the log likelihood for an M component mixed Gaussian distribution must be determined as represented by block 90. For example, in a two-component, mixed Gaussian distribution the log likelihood for the mixture of M Gaussian component distributions is given as follows:

$$L_2 = \sum_{i=1}^{n} \log(f_2(x)) \quad (11)$$

where $f_2(x)$ is given by equation (2).

Once the above two log likelihoods have been determined, a $X_2^2$ (chi-square) value must be computed as shown by block 92. The $X_2^2$ value is given generally by the following computation:

$$X_2^2 = -2 \log (L_1 - L_2) \quad (12)$$

for a two-component distribution, and $$X_2^2 = -2 \log (L_{M-1} - L_M) \quad (13)$$

for a M-component distribution, which is an asymptotically distributed chi-square on 2 degrees of freedom.

The $X_2^2$ value is evaluated as shown by decision block 94 to determine whether it is greater than the empirically determined value, which in the preferred embodiment has been selected as 5.99. If yes, then the M Gaussian distribution is a better fit than a $M-1$ Gaussian distribution, as shown by conclusion block 96, for the actual data generated for the stored pixel gray levels.

However, if the $X_2^2$ value is not sufficiently large, then the M value is rejected as shown by conclusion box 98. At that point, the conclusion is reached that the empirical distribution contains only M−1 component distribution.

As mentioned above, in conjunction with the discussion of FIGS. 1 and 2, the preferred embodiment of the means and method of the present invention may be utilized for analyzing the hair density in a human head area 12. In conjunction with this preferred embodiment, the following computer program may be utilized to perform the steps as generally set forth in the flowcharts illustrated in FIGS. 7, 8 and 9 to provide a multiple-component mixed Gaussian distribution as generally illustrated in FIG. 6 to match the frequency distribution or histogram of the actual data of the selected field as illustrated in FIG. 5.

```
$LARGE
$NOFLOATCALLS
$D066
$NOTSTRICT
$STORAGE.2
C
C
C
C
C
C
C
C    A GENERAL ALGORITHM FOR COMPUTING THE LIKELIHOOD AND DENSITY
C    OF A MIXTURE OF UNIVARIATE AND MULTIVARIATE NORMAL DISTRIBUTIONS
C
C
C
C
       IMPLICIT REAL*8(A-H,O-Z)
       DIMENSION SIGMAI(55),WRK(10),U(5,10),U1(10),P(5),X(500,5),
      *D(10),DS(1),X1(10),UHAT(5,10),UHAT1(10),
      *PHAT(5),SIGMA(55),SIGMAH(100),XXTOT(100),G(5),XXT(100),
      *UUT(100),UUTOT(100),UT(10),SUMX(10),DDT(100),DDTOT(100),
      *PI(500,5),RI(500),X9(10),X2(50),IFREQ(50)
       CHARACTER*80 TITLE1,TITLE2,FNS,FNAME,FNAME2,NFMT
       CHARACTER*8 XAXIS,YAXIS
       CHARACTER*3 INITSC,CLRSCR
       CHARACTER*2 EXITSC,JUNK
       CHARACTER YESNO
   1   FORMAT(I4)
   2   FORMAT(10F5.0)
   3   FORMAT(A80)
       WRITE(*,*)'ENTER 1 FOR FILE INPUT OR 2 FOR TERMINAL'
       READ(*,1)IFILE
       IF(IFILE.EQ.2)GOTO 404
       WRITE(*,*)'ENTER NAME OF SETUP FILE IN QUOTES'
       READ(*,3)FNS
       OPEN(1,FILE=FNS)
       READ(1,11)TITLE1
       READ(1,11)TITLE2
       READ(1,12)XAXIS
       READ(1,12)YAXIS
       READ(1,11)FNAME
       READ(1,11)FNAME2
       READ(1,16)JUNK
       READ(1,13)IGROUP,N,NC,NVAR,ISCORE,ILOG,IBAYES,KCONT,IHIST,NBIN,
     *  NOEST
       RNVAR=NVAR
       RN=N
       C=0.001D0
       RNEW=0.0D0
       READ(1,16)JUNK
       DO 19 I=1,NC
  19   READ(1,*)(U(I,J),J=1,NVAR)
```

```
            READ(1,16)JUNK
            READ(1,*)RMIN,RMAX                      -24-
            READ(1,16)JUNK
            READ(1,*)RMISS
11          FORMAT(/A80)
12          FORMAT(/A8)
13          FORMAT(20I4)
14          FORMAT(15F10.0)
16          FORMAT(A80)
            CLOSE(1)
            GO TO 18
404         WRITE(*,*) 'ENTER TITLE 1 IN QUOTES'
            READ(*,*) TITLE1
            WRITE(*,*) 'ENTER TITLE 2 IN QUOTES'
            READ(*,*) TITLE2
            WRITE(*,*) 'ENTER X-AXIS NAME IN QUOTES'
            READ(*,*) XAXIS
            WRITE(*,*) 'ENTER Y-AXIS NAME IN QUOTES'
            READ(*,*) YAXIS
            WRITE(*,*) 'ENTER INPUT FILE NAME IN QUOTES'
            READ(*,*) FNAME
            WRITE(*,*) 'ENTER OUTPUT HP PLOT FILE NAME IN QUOTES'
            READ(*,*) FNAME2
            WRITE(*,*)'ENTER 1 FOR UNGROUPED OR 2 FOR GROUPED DATA'
            READ(*,1)IGROUP
            WRITE(*,*) 'ENTER SAMPLE SIZE'
            READ(*,1)N
            WRITE(*,*) 'ENTER NUMBER OF COMPONENT DISTRIBUTIONS'
            READ(*,1)NC
            WRITE(*,*) 'ENTER NUMBER OF VARIABLES'
            READ(*,1)NVAR
            WRITE(*,*) 'ENTER 0 OR 1 FOR INDIVIDUAL SUBJECT CLASSIFICATION'
            READ(*,1)ISCORE
            WRITE(*,*) 'ENTER 0 OR 1 FOR LOG TRANSFORMATION'
            READ(*,1)ILOG
            WRITE(*,*)'ENTER 1 TO FIX THE CONTROL MEAN ELSE 0'
            READ(*,1)IBAYES
            IF(IBAYES.EQ.1)WRITE(*,*)'ENTER WHICH COMPONENT TO FIX'
            IF(IBAYES.EQ.1)READ(*,1)KCONT
            WRITE(*,*)'ENTER 1 TO SORT DATA INTO HISTOGRAM ELSE 0'
            READ(*,1)IHIST
            IF(IHIST.EQ.1)WRITE(*,*)'ENTER NUMBER OF BINS'
            IF(IHIST.EQ.1)READ(*,1)NBIN
C
C     INITIALIZE PARAMETERS
C
      C=0.001D00
      RNVAR=NVAR
      RN=N
      DO 200 I=1,NC
            WRITE(*,661)NVAR,I
661         FORMAT('ENTER ',I2,' MEAN(S) FOR COMPONENT',I2,' (5 COLS EACH)')
200   READ(*,2)(U(I,J),J=1,NVAR)
      NS=RNVAR*(RNVAR+1.0D0)/2.0D0
      WRITE(*,662)NS
662         FORMAT('ENTER ',I2,' ELEMENT(S) OF COVARIANCE MATRIX (5 COLS)')
      READ(*,2)(SIGMA(L),L=1,NS)
      NP=NC-1
            WRITE(*,*) 'ENTER ',NP,' PROPORTION(S) (5 COLS EACH)'
      READ(*,2)(P(I),I=1,NP)
```

```
        RNEW=0.0D0
        WRITE(*,*)'ENTER INPUT FORMAT STATEMENT IN QUOTES'
        READ(*,*)NFMT
        WRITE(*,*)'ENTER MIN AND MAX FOR X AXIS (5 COLS EACH)'
        READ(*,2)RMIN,RMAX
        WRITE(*,*)'ENTER MISSING VALUE CODE'
        READ(*,2)RMISS
18      CONTINUE
        DO 290 J=1,NVAR
290     SUMX(J)=0.0D0
        OPEN(3,FILE=FNAME)
        OPEN(4,FILE='MIXOUT DAT')
        L=0
        DO 240 I=1,N
        IF(IGROUP.EQ.1)R9=1.0D0
        IF(IGROUP.EQ.1)READ(3,NFMT)(X9(J),J=1,NVAR)
        IF(IGROUP.EQ.2)READ(3,NFMT)(X9(J),J=1,NVAR),R9
        DO 17 J=1,NVAR
17      IF(X9(J).EQ.RMISS)GOTO 240
        L=L+1
        RNEW=RNEW+R9
        RI(L)=R9
        DO 240 J=1,NVAR
        IF(ILOG.NE.1)X(L,J)=X9(J)
        IF(ILOG.EQ.1)X(L,J)=DLOG(X9(J))
        SUMX(J)=SUMX(J)+X(L,J)*RI(L)
240     CONTINUE
        N=L
        RN=N
        CLOSE(3)
        IF(IHIST.NE.1)GOTO 2020
        RBIN=NBIN
        XINT=RMIN
        RINT=(RMAX-RMIN)/RBIN
        NBINP1=NBIN+1
        DO 902 J=1,NBINP1
        IFREQ(J)=0
        R1=XINT-.5D0*RINT
        R2=XINT+.5D0*RINT
        DO 901 I=1,N
        IF(X(I,1).GE.R1.AND.X(I,1).LT.R2)IFREQ(J)=IFREQ(J)+RI(I)
901     CONTINUE
        X2(J)=R1+.5D0*RINT
        XINT=R2+.5D0*RINT
902     CONTINUE
        DO 903 I=1,NBINP1
        RI(I)=IFREQ(I)
903     X(I,1)=X2(I)
        N=NBINP1
2020    CONTINUE
        DO 15 I=1,24
15      WRITE(*,*)
        WRITE(4,*)
        WRITE(4,*)
        WRITE(4,*)
        WRITE(*,16)TITLE1
        WRITE(*,*)
        WRITE(*,16)TITLE2
        WRITE(4,16)TITLE1
        WRITE(4,*)
```

```
      WRITE(4,16)TITLE2
      WRITE(*,*)
      WRITE(*,*)
      WRITE(*,*)
      WRITE(*,*)
      WRITE(*,*)
      WRITE(4,*)
      WRITE(4,*)
      WRITE(4,*)
      WRITE(4,*)
      WRITE(4,*)
      DO 291 J=1,NVAR
  291 UT(J)=SUMX(J)/RNEW
      SUM=0.0D0
      DO 201 I=1,NP
  201 SUM=SUM+P(I)
      P(NC)=1.0D0-SUM
      ITER=0
    9 ITER=ITER+1
      RLIKE2=0.0D0
      RLIKE1=0.0D0
      WRITE(*,2000)ITER
      WRITE(4,2000)ITER
 2000 FORMAT(////' ITERATION ',I4/)
      DO 202 I=1,NC
      WRITE(*,99)I,(U(I,J),J=1,NVAR)
      WRITE(4,99)I,(U(I,J),J=1,NVAR)
  202 CONTINUE
   99 FORMAT(/' COMPONENT',I4/' MEANS   ',10F10.4/)
      WRITE(*,204)(P(I),I=1,NP)
      WRITE(4,204)(P(I),I=1,NP)
  204 FORMAT(/' PROPORTIONS ',5F10.4/)
      WRITE(*,1000)
      WRITE(4,1000)
 1000 FORMAT(/' COVARIANCE MATRIX '/)
      L1=0
      L=1
      DO 205 I=1,NVAR
      L1=L1+I
      WRITE(*,206)(SIGMA(L2),L2=L,L1)
      WRITE(4,206)(SIGMA(L2),L2=L,L1)
  206 FORMAT(10F10.4)
  205 L=L1+1
      DO 299 I=1,NS
  299 SIGMAI(I)=SIGMA(I)
C
C     COMPUTE DENSITY FUNCTION
C
      L=0
      DO 5 L1=1,NVAR
      DO 5 L2=1,NVAR
      L=L+1
      DDTOT(L)=0.0D0
    5 XXTOT(L)=0.0D0
      RND2=RNVAR/2.0D0
      IF(NVAR.GT.1)CALL INVS(SIGMA,NVAR,DET,WRK)
      IF(NVAR.GT.1)TPII=1.0D0/(((2.0D0*3.141592654D0)**(RND2))
     1*DSQRT(DET))
      IF(NVAR.EQ.1)TPII=1.0D0/DSQRT(2.0D0*3.141592654D0*SIGMA(1))
      DO 280 K=1,NC
```

```
      PHAT(K)=0.00D0
      DO 280 J=1,NVAR
      UHAT(K,J)=0.00D0
 280  CONTINUE
      DO 10 I=1,N
      DO 220 J=1,NVAR
 220  X1(J)=X(I,J)
      F=0.00D0
      DO 222 K=1,NC
      DO 221 J=1,NVAR
 221  U1(J)=U(K,J)
      CALL SUBM(X1,U1,D,NVAR,1,0)
      IF(NVAR.GT.1)CALL GRMMT(D,SIGMA,DS,NVAR,1,1,WRK)
      IF(NVAR.EQ.1)DS(1)=D(1)*D(1)*(1.0D0/SIGMA(1))
      G(K)=P(K)*TPII*DEXP(-.50D0*DS(1))
      F=F+G(K)
 222  CONTINUE
      RLIKE2=RLIKE2+DLOG(F)*RI(I)
      DO 250 K=1,NC
      PI(I,K)=RI(I)*G(K)/F
      IF(K.GT.NP)GO TO 510
      PHAT(K)=PHAT(K)+RI(I)*G(K)/F
 510  CONTINUE
      DO 250 J=1,NVAR
      UHAT(K,J)=UHAT(K,J)+RI(I)*(G(K)/F)*X(I,J)
 250     IF(IBAYES.EQ.1.AND.K.EQ.KCONT)UHAT(KCONT,J)=U(KCONT,J)
      CALL MPYRT(X1,X1,XXT,NVAR,1,0,NVAR)
      SCALR=RI(I)
      CALL SCM(XXT,SCALR,XXT,NVAR,NVAR,0)
  10  CALL ADDM(XXT,XXTOT,XXTOT,NVAR,NVAR,0)
      SCALR=1.00D0/RNEW
      CALL SCM(XXTOT,SCALR,XXTOT,NVAR,NVAR,0)
      CALL SCM(PHAT,SCALR,PHAT,NP,1,0)
      SUMP=0.0D0
      DO 520 K=1,NP
 520  SUMP=SUMP+PHAT(K)
      PHAT(NC)=1.0D0-SUMP
      DO 300 K=1,NC
      DO 301 J=1,NVAR
 301  UHAT1(J)=UHAT(K,J)
      SCALR=1.00D0/(RNEW*PHAT(K))
      CALL SCM(UHAT1,SCALR,UHAT1,NVAR,1,0)
      DO 302 J=1,NVAR
      UHAT(K,J)=UHAT1(J)
 302     IF(IBAYES.EQ.1.AND.K.EQ.KCONT)UHAT(KCONT,J)=U(KCONT,J)
 300  CONTINUE
      L=0
      DO 400 L1=1,NVAR
      DO 400 L2=1,NVAR
      L=L+1
 400  UUTOT(L)=0.0D0
      DO 402 K=1,NC
      DO 401 J=1,NVAR
 401  UHAT1(J)=UHAT(K,J)
      CALL MPYRT(UHAT1,UHAT1,UUT,NVAR,1,0,NVAR)
      SCALR=PHAT(K)
      CALL SCM(UUT,SCALR,UUT,NVAR,NVAR,0)
 402  CALL ADDM(UUT,UUTOT,UUTOT,NVAR,NVAR,0)
      CALL SUBM(XXTOT,UUTOT,SIGMAH,NVAR,NVAR,0)
      CALL CHAMS(SIGMAH,SIGMAH,NVAR,0,1)
```

```
      IF(ISCORE.EQ.3)GOTO 4158
      IF(NOEST.EQ.1)GOTO 4158
    IFLAG=0
    DO 600 I=1,NS
    DIF=DABS(SIGMA(I)-SIGMAH(I))
    IF(DIF.GT.C)IFLAG=1
600 SIGMA(I)=SIGMAH(I)
    DO 501 I=1,NC
    DIF=DABS(P(I)-PHAT(I))
    IF(DIF.GT.C)IFLAG=1
    P(I)=PHAT(I)
    DO 501 J=1,NVAR
    DIF=DABS(U(I,J)-UHAT(I,J))
    IF(DIF.GT.C)IFLAG=1
501 U(I,J)=UHAT(I,J)
    IF(ITER.GT.100)IFLAG=0
    IF(IFLAG.EQ.1)GO TO 9
    WRITE(*,228)
    WRITE(4,228)
228 FORMAT(//'    ESTIMATION PHASE COMPLETED'//)
    WRITE(*,*)'HIT ANY KEY TO CONTINUE'
    READ(*,3)YESNO
4158    CONTINUE
    DO 60 I=1,N
    DO 61 J=1,NVAR
61  X1(J)=X(I,J)
    CALL SUBM(X1,UT,D,NVAR,1,0)
    CALL MPYRT(D,D,DDT,NVAR,1,0,NVAR)
    SCALR=RI(I)
    CALL SCM(DDT,SCALR,DDT,NVAR,NVAR,0)
60  CALL ADDM(DDT,DDTOT,DDTOT,NVAR,NVAR,0)
    SCALR=1.0D0/(RNEW-1.0D0)
    CALL SCM(DDTOT,SCALR,DDTOT,NVAR,NVAR,0)
    CALL CHAMS(DDTOT,DDTOT,NVAR,0,1)
    DO 194 K=1,NS
194 SIGMAH(K)=DDTOT(K)
    IF(NVAR.GT.1)CALL INVS(DDTOT,NVAR,DET,WRK)
    IF(NVAR.GT.1)TPII=1.0D0/(((2.0D0*3.141592654D0)**(NVAR/2.0D0))
   1*DSQRT(DET))
    IF(NVAR.EQ.1)TPII=1.0D0/DSQRT(2.0D0*3.141592654D0*DDTOT(1))
    DO 50 I=1,N
    DO 51 J=1,NVAR
51  X1(J)=X(I,J)
    CALL SUBM(X1,UT,D,NVAR,1,0)
    IF(NVAR.GT.1)CALL GRMMT(D,DDTOT,DS,NVAR,1,1,WRK)
    IF(NVAR.EQ.1)DS(1)=D(1)*D(1)*(1.0D0/DDTOT(1))
    GT=TPII*DEXP(-.5D0*DS(1))
    RLIKE1=RLIKE1+DLOG(GT)*RI(I)
50  CONTINUE
    WRITE(*,995)(UT(J),J=1,NVAR)
    WRITE(4,995)(UT(J),J=1,NVAR)
995 FORMAT(////' OVERALL MEANS   ',10F10.4)
    WRITE(*,6000)
    WRITE(4,6000)
6000 FORMAT(/' OVERALL COVARIANCE MATRIX '//)
    L1=0
    L=1
    DO 805 I=1,NVAR
    L1=L1+I
    WRITE(*,206)(SIGMAH(L2),L2=L,L1)
```

```
      WRITE(4,206)(SIGMAH(L2),L2=L,L1)
  805 L=L1+1
      CHI=-2.0D0*(RLIKE1-RLIKE2)
      WRITE(*,55)RLIKE1,RLIKE2,CHI
      WRITE(4,55)RLIKE1,RLIKE2,CHI
   55 FORMAT(////' LIKELIHOOD FOR UNIMODAL DISTRIBUTION ',F10.3/
     *' LIKELIHOOD FOR MIXTURE DISTRIBUTION   ',F10.3/
     */' CHI-SQUARE FOR IMPROVEMENT IN FIT     ',F10.3////)
      IF(ISCORE.EQ.0)GO TO 1111
      WRITE(*,4444)NVAR,NC
      WRITE(4,4444)NVAR,NC
 4444 FORMAT(////' SUBJECT',5X,I4,' VARIABLES',5X,I4,' PROBABILITIES'///)
      DO 2222 I=1,N
      WRITE(*,3333)I,(X(I,J),J=1,NVAR),(PI(I,K),K=1,NC)
      WRITE(4,3333)I,(X(I,J),J=1,NVAR),(PI(I,K),K=1,NC)
 2222 CONTINUE
      WRITE(*,*)
 3333 FORMAT(I4,10F10.4)
 1111 CONTINUE
      XMAX=RMAX
      XMIN=RMIN
      IF(NVAR.GT.1)GO TO 4545
 4546 WRITE(*,*) 'ENTER NUMBER OF BINS FOR HISTOGRAM'
      READ(*,1)NBIN
      IF(ITRY.NE.1)GOTO 4547
      WRITE(*,*)'DO YOU WANT TO CHANGE XMIN AND XMAX? 1=Y 2=N'
      READ(*,1)IX
      IF(IX.EQ.2)GOTO 4547
      WRITE(*,*)'ENTER NEW MIN FOR X-AXIS'
      READ(*,2)RMIN
      WRITE(*,*)'ENTER NEW MAX FOR X-AXIS'
      READ(*,2)RMAX
      XMAX=RMAX
      XMIN=RMIN
 4547 OPEN(2,FILE=FNAME2)
      CALL INITGR(1)
      IF(NVAR.EQ.1.AND.NC.EQ.2.AND.CHI.GT.5.0D0)CALL TWO(CHI,X,U,SIGMA,
     *P,N,NBIN,TITLE1,TITLE2,XAXIS,YAXIS,RI,RNEW,RMIN,RMAX)
      IF(NVAR.EQ.1.AND.CHI.LE.5.0D0)CALL ONE(CHI,X,UT,SIGMAH,N,
     *NBIN,TITLE1,TITLE2,XAXIS,YAXIS,RI,RNEW,RMIN,RMAX)
      IF(NVAR.EQ.1.AND.NC.EQ.3.AND.CHI.GT.5.0D0)CALL THREE(CHI,X,U,SIGMA,
     *P,N,NBIN,TITLE1,TITLE2,XAXIS,YAXIS,RI,RNEW,RMIN,RMAX)
      READ(*,3) YESNO
      CALL CLOSEG
C     WRITE(*,*) INITSC
C     WRITE(*,*) CLRSCR
C     WRITE(*,*) EXITSC
 4545 CONTINUE
      CLOSE(2)
      WRITE(*,*)'ENTER 1 TO TRY A NEW PLOT ELSE 0'
      READ(*,1)ITRY
      RMIN=XMIN
      RMAX=XMAX
      IF(ITRY.EQ.1)GOTO 4546
      CLOSE(4)
      STOP
      END
      SUBROUTINE CLS
      IMPLICIT REAL*8(A-H,O-Z)
      DO 1 I=1,24
```

```
        WRITE(*,*)
1       CONTINUE
        RETURN
        END
$DEBUG
$LARGE
$NOFLOATCALLS
$0066
$NOTSTRICT
$STORAGE:2
      SUBROUTINE TWO(CHI,X,U,SIGMA,P,N,NBIN,TITLE1,TITLE2,XAXIS,YAXIS,
     1RI,RNEW,RMIN,RMAX)
        IMPLICIT REAL*8(A-H,O-Z)
      DIMENSION SIGMA(1),P(1),U(5,10),X(500,5),R(21),IFREQ(21),RI(1)
        CHARACTER*80 TITLE1,TITLE2,BF1,BF2,BF3,BF4,BF5
        CHARACTER*8 XAXIS,YAXIS
        CHARACTER*1 ESC,BR
        RBIN=NBIN
        ESC=CHAR(3)
      NG=N
      XM1=U(1,1)
      XM2=U(2,1)
      VAR=DSQRT(SIGMA(1))
      P1=P(1)
      XMAX=RMAX
      XMIN=RMIN
        YMIN=0.0D0
      RINT=(XMAX-XMIN)/RBIN
        NBINP1=NBIN+1
      JMAX=0
      DO 902 J=1,NBINP1
      IFREQ(J)=0
      R1=RMIN-.5D0*RINT
      R2=RMIN+.5D0*RINT
      R(J)=RMIN
      DO 901 I=1,NG
      IF(X(I,1).GE.R1.AND.X(I,1).LT.R2)IFREQ(J)=IFREQ(J)+RI(I)
901   CONTINUE
      IF(IFREQ(J).GT.JMAX)JMAX=IFREQ(J)
      RMIN=R2+.5D0*RINT
902   CONTINUE
        YMAX=JMAX*2
        CALL SETUP(XMAX,XMIN,YMAX,YMIN,TITLE1,TITLE2,XAXIS,YAXIS)
      RJMIN=0
      XO=XMIN
      RINC=(XMAX-XMIN)/100.0D0
      RNG=NG
        CALL LPLOT(XMIN,YMIN,XMAX,XMIN,YMAX,YMIN,3)
      DO 224 J=1,NBINP1
        XP=R(J)
        YP=IFREQ(J)
224   CALL CPLOT(XP,YP,XMAX,XMIN,YMAX,YMIN)
      CALL LPLOT(XMIN,YMIN,XMAX,XMIN,YMAX,YMIN,3)
      XO=XMIN-RINC
      Z=(XO-XM1)/VAR
      PROBM1=PHI(Z)
      XO=XMIN
      DO 226 I=1,100
      Z=(XO-XM1)/VAR
      PROB=PHI(Z)
        IF(PROB.LE.PROBM1)DPROB=0.0D0
```

```
       IF(PROB.GT.PROBM1)DPROB=(PROB-PROBM1)*P1*RNEW*(RINT/RINC)
       PROBM1=PROB
          CALL LPLOT(XO,DPROB,XMAX,XMIN,YMAX,YMIN,2)
  226  XO=XO+RINC
       XO=XMIN-RINC
       Z=(XO-XM2)/VAR
       PROBM1=PHI(Z)
       XO=XMIN
       DO 228 I=1,100
       Z=(XO-XM2)/VAR
       PROB=PHI(Z)
       DPROB=(PROB-PROBM1)*(1.0D0-P1)*RNEW*(RINT/RINC)
       PROBM1=PROB
          CALL LPLOT(XO,DPROB,XMAX,XMIN,YMAX,YMIN,2)
  228  XO=XO+RINC
       XO=XMIN-RINC
       Z=(XO-XM1)/VAR
       PROBM1=PHI(Z)
       XO=XMIN
       DO 726 I=1,100
       Z=(XO-XM1)/VAR
       PROB=PHI(Z)
       DPROB=(PROB-PROBM1)*P1*RNEW*(RINT/RINC)
       PROBM1=PROB
       IF(PROB.GT..05D0.AND.PROB.LT..95D0)CALL LPLOT(XO,RJMIN,XMAX,XMIN,
      1 YMAX,YMIN,3)
       IF(PROB.GT..05D0.AND.PROB.LT..95D0)CALL LPLOT(XO,DPROB,XMAX,XMIN,
      1 YMAX,YMIN,2)
  726  XO=XO+RINC
       XO=XMIN-RINC
       Z=(XO-XM2)/VAR
       PROBM1=PHI(Z)
       XO=XMIN
       DO 826 I=1,100
       Z=(XO-XM2)/VAR
       PROB=PHI(Z)
       DPROB=(PROB-PROBM1)*(1.0D0-P1)*RNEW*(RINT/RINC)
       PROBM1=PROB
       IF(PROB.GT..05D0.AND.PROB.LT..95D0)CALL LPLOT(XO,RJMIN,XMAX,XMIN,
      1YMAX,YMIN,3)
       IF(PROB.GT..05D0.AND.PROB.LT..95D0)CALL LPLOT(XO,DPROB,XMAX,XMIN,
      1YMAX,YMIN,2)
  826  XO=XO+RINC
       P2=1.D0-P1
         BR='"'
       WRITE(BF1,33)BR,XM1,XM2,BR
       WRITE(BF2,34)BR,P1,P2,BR
       WRITE(BF3,35)BR,VAR,BR
       WRITE(BF4,36)BR,RNEW,BR
       WRITE(BF5,37)BR,CHI,BR
       CALL MOVTCA(350,10)
       CALL TEXT('/MEANS        /')
       CALL TEXT(BF1)
       CALL MOVTCA(350,20)
       CALL TEXT('/PROPORTIONS/')
       CALL TEXT(BF2)
       CALL MOVTCA(350,30)
       CALL TEXT('/SD           /')
       CALL TEXT(BF3)
       CALL MOVTCA(350,40)
       CALL TEXT('/TOTAL N    /')
       CALL TEXT(BF4)
```

-32-

```
            CALL MOVTCA(350,50)
            CALL TEXT('/CHI SQUARE /')
            CALL TEXT(BF5)                          -33-
            CALL DELTCU
   33       FORMAT(A1,2F10.3,A1)
   34       FORMAT(A1,2F10.3,A1)
   35       FORMAT(A1,10X,F10.3,A1)
   36       FORMAT(A1,10X,F10.0,A1)
   37       FORMAT(A1,10X,F10.3,A1)
            WRITE(2,781)XM1,XM2,ESC,P1,P2,ESC
  781   FORMAT('PU,200,250;LBMEANS',6X,2F10.3,A1,
       1'PU,200,240;LBPROPORTIONS',2F10.3,A1)
            WRITE(2,783)VAR,ESC
  783       FORMAT('PU,200,230;LBSD          ',10X,F10.3,A1)
            WRITE(2,782)RNEW,ESC,CHI,ESC
  782       FORMAT('PU,200,220;LBTOTAL N     ',10X,F10.0,A1,
       1'PU,200,210;LBCHI SQUARE ',10X,F10.3,A1,'PU,0,0;')
            RETURN
            END
C::::::::::::::::::::::::::::::::::::::::::::::::::::::::::::::::::::
C:::::NORMAL PROBABILITY DISTRIBUTION FUNCTION (INTERCEPT)::::::::::::
C::::::::::::::::::::::::::::::::::::::::::::::::::::::::::::::::::::
            FUNCTION PHI(Z)
            IMPLICIT REAL*8(A-H,O-Z)
            IF(Z.LT.-10.0D0)GO TO 1
            IF(Z.GT.10.0D0)GO TO 2
            Z2=DABS(Z)
            ORD=(DEXP(-Z*Z/2.0D0))/2.506628275D0
            E=1.0D0/(1.0D0+0.2316418D0*Z2)
            G=((((1.330274429D0*E-1.821255978D0)*E+1.781477937D0)*E
           *-0.356563782D0)*E+0.319381530D0)*E
            G=G*ORD
            IF(Z.LE.0.0D0)PHI=G
            IF(Z.GT.0.0D0)PHI=1.0D0-G
            RETURN
    1       PHI=0.000000001D0
            RETURN
    2       PHI=0.999999999D0
            RETURN
            END
            SUBROUTINE THREE(CHI,X,U,SIGMA,P,N,NBIN,TITLE1,TITLE2,XAXIS,YAXIS,
           1RI,RNEW,RMIN,RMAX)
            IMPLICIT REAL*8(A-H,O-Z)
            DIMENSION SIGMA(1),P(1),U(5,10),X(500,5),R(21),IFREQ(21),
           *RI(1)
            CHARACTER*80 TITLE1,TITLE2,BF1,BF2,BF3,BF4,BF5
            CHARACTER*8 XAXIS,YAXIS
            CHARACTER*1 ESC,BR
            ESC=CHAR(3)
            NG=N
            XM1=U(1,1)
            XM2=U(2,1)
            XM3=U(3,1)
            VAR=DSQRT(SIGMA(1))
            P1=P(1)
            P2=P(2)
            P3=1.D0-(P1+P2)
            RBIN=NBIN
            XMAX=RMAX
            XMIN=RMIN
            YMIN=0.0D0
```

```
      NBINP1=NBIN+1
      RINT=(XMAX-XMIN)/RBIN
      JMAX=0
      DO 902 J=1,NBINP1
      IFREQ(J)=0
      R1=RMIN-.5D0*RINT
      R2=RMIN+.5D0*RINT
      R(J)=RMIN
      DO 901 I=1,NG
      IF(X(I,1).GE.R1.AND.X(I,1).LT.R2)IFREQ(J)=IFREQ(J)+RI(I)
901   CONTINUE
      IF(IFREQ(J).GT.JMAX)JMAX=IFREQ(J)
      RMIN=R2+.5D0*RINT
902   CONTINUE
      YMAX=JMAX*2
        CALL SETUP(XMAX,XMIN,YMAX,YMIN,TITLE1,TITLE2,XAXIS,YAXIS)
      XO=XMIN
      RINC=(XMAX-XMIN)/100.0D0
      RNG=NG
        CALL LPLOT(XMIN,YMIN,XMAX,XMIN,YMAX,YMIN,3)
      DO 224 J=1,NBINP1
        XP=R(J)
        YP=IFREQ(J)
224     CALL CPLOT(XP,YP,XMAX,XMIN,YMAX,YMIN)
        CALL LPLOT(XMIN,YMIN,XMAX,XMIN,YMAX,YMIN,3)
      XO=XMIN-RINC
      Z=(XO-XM1)/VAR
      PROBM1=PHI(Z)
      XO=XMIN
      DO 226 I=1,100
      Z=(XO-XM1)/VAR
      PROB=PHI(Z)
      DPROB=(PROB-PROBM1)*P1*RNEW*(RINT/RINC)
      PROBM1=PROB
        CALL LPLOT(XO,DPROB,XMAX,XMIN,YMAX,YMIN,2)
226   XO=XO+RINC
      XO=XMIN-RINC
      Z=(XO-XM2)/VAR
      PROBM1=PHI(Z)
      XO=XMIN
      DO 228 I=1,100
      Z=(XO-XM2)/VAR
      PROB=PHI(Z)
      DPROB=(PROB-PROBM1)*P2*RNEW*(RINT/RINC)
      PROBM1=PROB
        CALL LPLOT(XO,DPROB,XMAX,XMIN,YMAX,YMIN,2)
228   XO=XO+RINC
      XO=XMIN-RINC
      Z=(XO-XM3)/VAR
      PROBM1=PHI(Z)
      XO=XMIN
      DO 28 I=1,100
      Z=(XO-XM3)/VAR
      PROB=PHI(Z)
      DPROB=(PROB-PROBM1)*P3*RNEW*(RINT/RINC)
      PROBM1=PROB
        CALL LPLOT(XO,DPROB,XMAX,XMIN,YMAX,YMIN,2)
28    XO=XO+RINC
      XO=XMIN-RINC
      Z=(XO-XM1)/VAR
```

```
      PROBM1=PHI(Z)
      XO=XMIN
      DO 726 I=1,100
      Z=(XO-XM1)/VAR
      PROB=PHI(Z)
      DPROB=(PROB-PROBM1)*P1*RNEW*(RINT/RINC)
      PROBM1=PROB
      IF(PROB.GT..05D0.AND.PROB.LT..95D0)CALL LPLOT(XO,YMIN,XMAX,XMIN,
     *YMAX,YMIN,3)
      IF(PROB.GT..05D0.AND.PROB.LT..95D0)CALL LPLOT(XO,DPROB,XMAX,XMIN,
     *YMAX,YMIN,2)
  726 XO=XO+RINC
      XO=XMIN-RINC
      Z=(XO-XM2)/VAR
      PROBM1=PHI(Z)
      XO=XMIN
      DO 826 I=1,100
      Z=(XO-XM2)/VAR
      PROB=PHI(Z)
      DPROB=(PROB-PROBM1)*P2*RNEW*(RINT/RINC)
      PROBM1=PROB
      IF(PROB.GT..05D0.AND.PROB.LT..95D0)CALL LPLOT(XO,YMIN,XMAX,XMIN,
     *YMAX,YMIN,3)
      IF(PROB.GT..05D0.AND.PROB.LT..95D0)CALL LPLOT(XO,DPROB,XMAX,XMIN,
     *YMAX,YMIN,2)
  826 XO=XO+RINC
      XO=XMIN-RINC
      Z=(XO-XM3)/VAR
      PROBM1=PHI(Z)
      XO=XMIN
      DO 26 I=1,100
      Z=(XO-XM3)/VAR
      PROB=PHI(Z)
      DPROB=(PROB-PROBM1)*P3*RNEW*(RINT/RINC)
      PROBM1=PROB
      IF(PROB.GT..05D0.AND.PROB.LT..95D0)CALL LPLOT(XO,YMIN,XMAX,XMIN,
     *YMAX,YMIN,3)
      IF(PROB.GT..05D0.AND.PROB.LT..95D0)CALL LPLOT(XO,DPROB,XMAX,XMIN,
     *YMAX,YMIN,2)
   26 XO=XO+RINC
        BR='"'
      WRITE(BF1,33)BR,XM1,XM2,XM3,BR
      WRITE(BF2,34)BR,P1,P2,P3,BR
      WRITE(BF3,35)BR,VAR,BR
      WRITE(BF4,36)BR,RNEW,BR
      WRITE(BF5,37)BR,CHI,BR
      CALL MOVTCA(300,10)
      CALL TEXT('/MEANS       /')
      CALL TEXT(BF1)
      CALL MOVTCA(300,20)
      CALL TEXT('/PROPORTIONS/')
      CALL TEXT(BF2)
      CALL MOVTCA(300,30)
      CALL TEXT('/SD          /')
      CALL TEXT(BF3)
      CALL MOVTCA(300,40)
      CALL TEXT('/TOTAL N    /')
      CALL TEXT(BF4)
      CALL MOVTCA(300,50)
      CALL TEXT('/CHI SQUARE /')
```

```
            CALL TEXT(BFS)
            CALL DELTCU
33          FORMAT(A1,3F10.3,A1)
34          FORMAT(A1,3F10.3,A1)
35          FORMAT(A1,20X,F10.3,A1)
36          FORMAT(A1,20X,F10.0,A1)
37          FORMAT(A1,20X,F10.3,A1)
         WRITE(2,781)XM1,XM2,XM3,ESC,P1,P2,P3,ESC
  781 FORMAT('PU,200,250;LBMEANS',6X,3F7.2,A1,
     1'PU,200,240;LBPROPORTIONS',3F7.2,A1)
         WRITE(2,783)VAR,ESC
783        FORMAT('PU,200,230;LBSD           ',14X,F7.2,A1)
         WRITE(2,782)RNEW,ESC,CHI,ESC
  782      FORMAT('PU,200,220;LBTOTAL N    ',14X,F7.0,A1,
     1'PU,200,210;LBCHI SQUARE ',14X,F7.2,A1,'PU,0,0;')
         RETURN
         END
         SUBROUTINE ONE(CHI,X,UT,SIGMAH,N,NBIN,TITLE1,TITLE2,XAXIS,YAXIS,
     1RI,RNEW,RMIN,RMAX)
            IMPLICIT REAL*8(A-H,O-Z)
         DIMENSION SIGMAH(1),UT(10),X(500,5),R(21),IFREQ(21),RI(1),
     *RFREQ(21)
            CHARACTER*80 TITLE1,TITLE2,BF1,BF2,BF3,BF4,BF5
            CHARACTER*8 XAXIS,YAXIS
            CHARACTER*1 ESC,BR
            ESC=CHAR(3)
            RBIN=NBIN
            NBINP1=NBIN+1
         NG=N
         XM1=UT(1)
         VAR=DSQRT(SIGMAH(1))
         P1=1.0D0
            XMAX=RMAX
            XMIN=RMIN
            YMIN=0.0D0
            RBIN=NBIN
         RINT=(XMAX-XMIN)/RBIN
         JMAX=0
         DO 902 J=1,NBINP1
         IFREQ(J)=0
         R1=RMIN-.5D0*RINT
         R2=RMIN+.5D0*RINT
         R(J)=RMIN
         DO 901 I=1,NG
         IF(X(I,1).GE.R1.AND.X(I,1).LT.R2)IFREQ(J)=IFREQ(J)+RI(I)
  901 CONTINUE
         IF(IFREQ(J).GT.JMAX)JMAX=IFREQ(J)
         RMIN=R2+.5D0*RINT
  902 CONTINUE
            YMAX=JMAX*2
            CALL SETUP(XMAX,XMIN,YMAX,YMIN,TITLE1,TITLE2,XAXIS,YAXIS)
            CALL LPLOT(XMIN,YMIN,XMAX,XMIN,YMAX,YMIN,3)
         XO=XMIN
         RINC=(XMAX-XMIN)/100.0D0
         RNG=NG
         DO 224 J=1,NBINP1
         RFREQ(J)=IFREQ(J)
            XP=R(J)
            YP=IFREQ(J)
  224 CALL CPLOT(XP,YP,XMAX,XMIN,YMAX,YMIN)
```

```
      CALL LPLOT(XMIN,YMIN,XMAX,XMIN,YMAX,YMIN,3)
      XO=XMIN-RINC
      Z=(XO-XM1)/VAR
      PROBM1=PHI(Z)
      XO=XMIN
      DO 226 I=1,100
      Z=(XO-XM1)/VAR
      PROB=PHI(Z)
      DPROB=(PROB-PROBM1)*P1*RNEW*(RINT/RINC)
      PROBM1=PROB
      CALL LPLOT(XO,DPROB,XMAX,XMIN,YMAX,YMIN,2)
226   XO=XO+RINC
      XO=XMIN-RINC
      Z=(XO-XM1)/VAR
      PROBM1=PHI(Z)
      XO=XMIN
      DO 726 I=1,100
      Z=(XO-XM1)/VAR
      PROB=PHI(Z)
      DPROB=(PROB-PROBM1)*P1*RNEW*(RINT/RINC)
      PROBM1=PROB
      IF(PROB.GT..05D0.AND.PROB.LT..95D0)CALL LPLOT(XO,YMIN,XMAX,XMIN,
     *YMAX,YMIN,3)
      IF(PROB.GT..05D0.AND.PROB.LT..95D0)CALL LPLOT(XO,DPROB,XMAX,XMIN,
     *YMAX,YMIN,2)
726   XO=XO+RINC
      BR=''''
      WRITE(BF1,33)BR,XM1,BR
      WRITE(BF3,35)BR,VAR,BR
      WRITE(BF4,36)BR,RNEW,BR
      WRITE(BF5,37)BR,CHI,BR
      CALL MOVTCA(400,10)
      CALL TEXT('/MEAN      /')
      CALL TEXT(BF1)
      CALL MOVTCA(400,20)
      CALL TEXT('/SD        /')
      CALL TEXT(BF3)
      CALL MOVTCA(400,30)
      CALL TEXT('/TOTAL N   /')
      CALL TEXT(BF4)
      CALL MOVTCA(400,40)
      CALL TEXT('/CHI SQUARE /')
      CALL TEXT(BF5)
      CALL DELTCU
33    FORMAT(A1,F10.3,A1)
34    FORMAT(A1,F10.3,A1)
35    FORMAT(A1,F10.3,A1)
36    FORMAT(A1,F10.0,A1)
37    FORMAT(A1,F10.3,A1)
      WRITE(2,781)XM1,ESC,VAR,ESC
781   FORMAT('PU,250,250;LBMEAN',7X,F10.3,A1,
     1'PU,250,240;LBSD          ',F10.3,A1)
      WRITE(2,782)RNEW,ESC,CHI,ESC
782   FORMAT('PU,250,230;LBTOTAL N   ',F10.0,A1,
     1'PU,250,220;LBCHI SQUARE ',F10.3,A1,'PU,0,0;')
      RETURN
      END
      SUBROUTINE SETUP(XMAX,XMIN,YMAX,YMIN,TITLE1,TITLE2,
     *XAXIS,YAXIS)
      IMPLICIT REAL*8(A-H,O-Z)
```

```
      CHARACTER*80 TITLE1,TITLE2,BF1,BF2,BF3,BF4,BF5,BF6,BF7,BF8
      CHARACTER*8 XAXIS,YAXIS
      CHARACTER*3 INITSC,CLRSCR
      CHARACTER*1 ESC,BR
      CHARACTER*2 EXITSC
      BR='"'
      ESC=CHAR(3)
      DO 109 I=1,24
      WRITE(*,*)
109   CONTINUE
      RX1=XMIN+(XMAX-XMIN)/4.0D0
      RX2=XMIN+((XMAX-XMIN)/4.0D0)*2.D0
      RX3=XMIN+((XMAX-XMIN)/4.0D0)*3.D0
      RX4=XMIN+(XMAX-XMIN)
      RY1=YMIN+(YMAX-YMIN)/4.0D0
      RY2=YMIN+((YMAX-YMIN)/4.0D0)*2.D0
      RY3=YMIN+((YMAX-YMIN)/4.0D0)*3.D0
      RY4=YMAX
      WRITE(BF1,42)BR,RX1,BR
      WRITE(BF2,42)BR,RX2,BR
      WRITE(BF3,42)BR,RX3,BR
      WRITE(BF4,42)BR,RX4,BR
      WRITE(BF5,42)BR,RY1,BR
      WRITE(BF6,42)BR,RY2,BR
      WRITE(BF7,42)BR,RY3,BR
      WRITE(BF8,42)BR,RY4,BR
      CALL MOVABS(100,170)
      CALL LNABS(100,30)
      CALL MOVABS(100,170)
      CALL LNABS(500,170)
      IX11=(RX1-XMIN)/((XMAX-XMIN)/400.0D0)+100.0D0
      IY11=RY1/(YMAX/140.0D0)+30.0D0
      IX22=(RX2-XMIN)/((XMAX-XMIN)/400.0D0)+100.0D0
      IY22=RY2/(YMAX/140.0D0)+30.0D0
      IX33=(RX3-XMIN)/((XMAX-XMIN)/400.0D0)+100.0D0
      IY33=RY3/(YMAX/140.0D0)+30.0D0
      IX44=(RX4-XMIN)/((XMAX-XMIN)/400.0D0)+100.0D0
      IY44=RY4/(YMAX/140.0D0)+30.0D0
      IY11=200.0D0-IY11
      IY22=200.0D0-IY22
      IY33=200.0D0-IY33
      IY44=200.0D0-IY44
      CALL MOVTCA(170,180)
      CALL TEXT(BF1)
      CALL MOVTCA(270,180)
      CALL TEXT(BF2)
      CALL MOVTCA(370,180)
      CALL TEXT(BF3)
      CALL MOVTCA(470,180)
      CALL TEXT(BF4)
      CALL MOVTCA(40,140)
      CALL TEXT(BF5)
      CALL MOVTCA(40,110)
      CALL TEXT(BF6)
      CALL MOVTCA(40,80)
      CALL TEXT(BF7)
      CALL MOVTCA(40,50)
      CALL TEXT(BF8)
C     WRITE(BF1,40)BR,YAXIS,BR
      WRITE(BF2,40)BR,XAXIS,BR
```

```
         WRITE(BF3,41)BR,TITLE1,BR
         WRITE(BF4,41)BR,TITLE2,BR
40       FORMAT(A1,A8,A1)
41       FORMAT(A1,A78,A1)
42       FORMAT(A1,F5.1,A1)
C        CALL MOVTCA(10,100)
C        CALL TEXT(BF1)
         CALL MOVTCA(10,50)
         CALL TEXT('/F/')
         CALL MOVTCA(10,60)
         CALL TEXT('/R/')
         CALL MOVTCA(10,70)
         CALL TEXT('/E/')
         CALL MOVTCA(10,80)
         CALL TEXT('/Q/')
         CALL MOVTCA(10,90)
         CALL TEXT('/U/')
         CALL MOVTCA(10,100)
         CALL TEXT('/E/')
         CALL MOVTCA(10,110)
         CALL TEXT('/N/')
         CALL MOVTCA(10,120)
         CALL TEXT('/C/')
         CALL MOVTCA(10,130)
         CALL TEXT('/Y/')
         CALL MOVTCA(280,190)
         CALL TEXT(BF2)
         CALL MOVTCA(10,10)
         CALL TEXT(BF3)
         CALL MOVTCA(10,20)
         CALL TEXT(BF4)
         CALL BOX(1,1,635,195)
         CALL MOVABS(IX11,175)
         CALL LNABS(IX11,170)
         CALL MOVABS(IX22,175)
         CALL LNABS(IX22,170)
         CALL MOVABS(IX33,175)
         CALL LNABS(IX33,170)
         CALL MOVABS(IX44,175)
         CALL LNABS(IX44,170)
         CALL MOVABS(90,IX11)
         CALL LNABS(100,IX11)
         CALL MOVABS(90,IX22)
         CALL LNABS(100,IX22)
         CALL MOVABS(90,IX33)
         CALL LNABS(100,IX33)
         CALL MOVABS(90,IX44)
         CALL LNABS(100,IX44)
         WRITE(2,*) 'PU,0,0;PU,100,50;PD,100,250;PU,100,50,PD,300,50,'
         WRITE(2,*) 'PU,100,35;'
         WRITE(2,524)RX1,ESC,RX2,ESC,RX3,ESC,RX4,ESC
524      FORMAT('PU,130,35; LB',F5.1,A1,
     *          'PU,180,35; LB',F5.1,A1,
     *          'PU,230,35; LB',F5.1,A1,
     *          'PU,280,35; LB',F5.1,A1)
         WRITE(2,525)RY1,ESC,RY2,ESC,RY3,ESC,RY4,ESC
525      FORMAT('PU,40,100; LB',F5.1,A1,'PU,40,150; LB',F5.1,A1,
     *   'PU,40,200; LB',F5.1,A1,'PU,40,250; LB',F5.1,A1)
         WRITE(2,1) YAXIS,ESC
         WRITE(2,2) XAXIS,ESC
```

```
      WRITE(2,3) TITLE1,ESC
      WRITE(2,4) TITLE2,ESC
      WRITE(2,*) 'PU,5,5;PD,5,295;PD,395,295;PD,395,5;PD,5,5;PU,0,0;'
1     FORMAT('PU,10,175;LB',A8,A1)
2     FORMAT('PU,180,15;LB',A8,A1)
3     FORMAT('PU,10,280;LB',A80,A1)
4     FORMAT('PU,10,265;LB',A80,A1)
      RETURN
      END
      SUBROUTINE LPLOT(X,Y,XMAX,XMIN,YMAX,YMIN,IPEN)
      IMPLICIT REAL*8(A-H,O-Z)
      RX=(X-XMIN)/((XMAX-XMIN)/400.0D0)+100.0D0
      RY=Y/(YMAX/140.0D0)+30.0D0
      IX=RX
      IY=200.0D0-RY
      IF(IPEN.EQ.2)CALL LNABS(IX,IY)
      IF(IPEN.EQ.3)CALL MOVABS(IX,IY)
      IF(IPEN.EQ.2)WRITE(2,3)RX,RY
      IF(IPEN.EQ.3)WRITE(2,4)RX,RY
3     FORMAT('PD,',F10.3,',',F10.3,';')
4     FORMAT('PU,',F10.3,',',F10.3,';')
      RETURN
      END
      SUBROUTINE CPLOT(X,Y,XMAX,XMIN,YMAX,YMIN)
      IMPLICIT REAL*8(A-H,O-Z)
      RX=(X-XMIN)/((XMAX-XMIN)/400.0D0)+100.0D0
      RY=Y/(YMAX/140.0D0)+30.0D0
      IX1=RX
         IX2=RX-3
         IY1=200.0D0-RY
      IY2=(200.0D0-RY)+3
      CALL LNABS(IX1,IY1)
         CALL MOVTCA(IX2,IY2)
         CALL TEXT('/*/')
      WRITE(2,2)RX,RY
2     FORMAT('SM*;PD,',F10.3,',',F10.3,';SM;')
      RETURN
      END
$LARGE
$NOFLOATCALLS
$0066
$NOTSTRICT
$STORAGE:2
C                                                                    ADDM000
C                  **********************                            ADDM001
C                  *   SUBROUTINE   ADDM *                            ADDM002
C                  **********************                            ADDM003
C                                                                    ADDM004
C        ADD TWO MATRICES                                            ADDM005
C                                                                    ADDM006
C        CALL ADDM(A,B,C,M,N,MS)                                     ADDM007
C                                                                    ADDM008
C        A  .......... INPUT MATRIX, M BY N                          ADDM009
C        B  .......... INPUT MATRIX, M BY N                          ADDM010
C        C  .......... OUTPUT MATRIX, M BY N, RESULT OF ADDITION     ADDM011
C        M  .......... NUMBER OF ROWS IN A, EQUAL TO NUMBER OF ROWS IN B ADDM012
C        N  .......... NUMBER OF COLUMNS IN A, EQUAL TO NUMBER OF    ADDM013
C                      COLUMNS IN B                                  ADDM014
C        MS .......... STORAGE MODE OF A, EQUAL TO STORAGE MODE OF B ADDM015
C                                                                    ADDM016
      SUBROUTINE ADDM(A,B,C,M,N,MS)                                  ADDM017
      DOUBLE PRECISION A,B,C                                         ADDM018
```

```
      DIMENSION A(1),B(1),C(1)                                    ADDM019
      MMS=MS+1                                                    ADDM020
      GOTO(1,2,3,2,2),MMS                                         ADDM021
    1 K=M*N                                                       ADDM022
      GO TO 4                                                     ADDM023
    2 K=M*(M+1)/2                                                 ADDM024
      GO TO 4                                                     ADDM025
    3 K=M                                                         ADDM026
    4 DO 5 I=1,K                                                  ADDM027
    5 C(I)=A(I)+B(I)                                              ADDM028
      CONTINUE                                                    ADDM029
      IF(LTEST-1)6666,6667,6666                                   ADDM030
 6667 CONTINUE                                                    ADDM031
C     CALL DPRNT(C,M,N,MS,    6HADDM )                            ADDM032
 6666 RETURN                                                      ADDM033
      END                                                         ADDM034
C                                                                 SUBM000
C                                                                 SUBM001
C               **********************                            SUBM002
C               *  SUBROUTINE   SUBM *                            SUBM003
C               **********************                            SUBM004
C                                                                 SUBM005
C       SUBTRACT TWO MATRICES                                     SUBM006
C                                                                 SUBM007
C       CALL SUBM(A,B,C,M,N,MS)                                   SUBM008
C                                                                 SUBM009
C       A  .......... INPUT MATRIX, M BY N, MINUEND               SUBM010
C       B  .......... INPUT MATRIX, M BY N, SUBTRAHEND            SUBM011
C       C  .......... OUTPUT MATRIX, M BY N, RESULT OF SUBTRACTION SUBM012
C       M  .......... NUMBER OF ROWS IN A, EQUAL TO NUMBER OF ROWS IN B SUBM013
C       N  .......... NUMBER OF COLUMNS IN A, EQUAL TO NUMBER OF  SUBM014
C                     COLUMNS IN B                                SUBM015
C       MS .........  STORAGE MODE OF A, EQUAL TO STORAGE MODE OF B SUBM016
C                                                                 SUBM017
      SUBROUTINE SUBM(A,B,C,M,N,MS)                               SUBM018
      DOUBLE PRECISION A,B,C                                      SUBM019
      DIMENSION A(1),B(1),C(1)                                    SUBM020
      MMS=MS+1
      GOTO(1,2,3,2,2),MMS                                         SUBM021
    1 K=M*N                                                       SUBM022
      GO TO 4                                                     SUBM023
    2 K=M*(M+1)/2                                                 SUBM024
      GO TO 4                                                     SUBM025
    3 K=M                                                         SUBM026
    4 DO 5 I=1,K                                                  SUBM027
    5 C(I)=A(I)-B(I)                                              SUBM028
      CONTINUE                                                    SUBM029
      IF(LTEST-1)6666,6667,6666                                   SUBM030
 6667 CONTINUE                                                    SUBM031
C     CALL DPRNT(C,M,N,MS,    6HSUBM )                            SUBM032
 6666 RETURN                                                      SUBM033
      END                                                         SUBM034
C                                                                 GRMMT000
C                                                                 GRMMT001
C               **********************                            GRMMT002
C               *  SUBROUTINE  GRMMT *                            GRMMT003
C               **********************                            GRMMT004
C                                                                 GRMMT005
C       OBTAIN THE GRAMIAN MATRIX OF GENERALIZED PRODUCTS OF COLUMN GRMMT006
C       VECTORS OF A SPECIFIED MATRIX BY POST- AND PREMULTIPLYING A GRMMT007
C       METRIC MATRIX (SYMMETRIC OR DIAGONAL, MS=1,2) BY THE MATRIX GRMMT008
C       AND ITS TRANSPOSE                                         GRMMT009
C                                                                 GRMMT010
C       CALL GRMMT (A,B,C,M,N,MSB,W)
```

```
C                                                              GRMMT011
C         A .......... INPUT MATRIX, M BY N, GENERAL RECTANGULAR (MSA=0)GRMMT012
C         B .......... INPUT MATRIX, M BY M, METRIC MATRIX, SYMMETRIC ORGRMMT013
C                      DIAGONAL                                 GRMMT014
C         C .......... OUTPUT MATRIX, N BY N, GENERALIZED GRAMIAN,  GRMMT015
C                      SYMMETRIC (MSC=1)                        GRMMT016
C         M .......... NUMBER OF ROWS IN A                      GRMMT017
C         N .......... NUMBER OF COLUMNS IN A                   GRMMT018
C         MSB ........ STORAGE MODE OF B                        GRMMT019
C         W .......... WORKING VECTOR OF LENGTH M               GRMMT020
C                                                               GRMMT021
      SUBROUTINE GRMMT(A,B,C,M,N,MSB,W)                         GRMMT022
      IMPLICIT REAL*8(A-H,O-Z)                                  GRMMT023
      DIMENSION A(M,N),B(1),C(1),W(1)                           GRMMT024
      KC=0                                                      GRMMT031
      DO 100 I=1,N                                              GRMMT032
      KK=0                                                      GRMMT033
      DO 101 K=1,M                                              GRMMT034
      X=0.0D0                                                   GRMMT035
      IC=KK                                                     GRMMT036
      DO 102 L=1,K                                              GRMMT037
      IC=IC+1                                                   GRMMT038
  102 X=X+A(L,I)*B(IC)                                          GRMMT039
      IF (K .EQ. M) GO TO 104                                   GRMMT040
      J=K+1                                                     GRMMT041
      IC=IC+K                                                   GRMMT042
      DO 103 L=J,M                                              GRMMT043
      X=X+A(L,I)*B(IC)                                          GRMMT044
  103 IC=IC+L                                                   GRMMT045
  104 W(K)=X                                                    GRMMT046
  101 KK=KK+K                                                   GRMMT047
      DO 105 K=1,I                                              GRMMT048
      KC=KC+1                                                   GRMMT049
      X=0.0D0                                                   GRMMT050
      DO 106 L=1,M                                              GRMMT051
  106 X=X+A(L,K)*W(L)                                           GRMMT052
  105 C(KC)=X                                                   GRMMT053
  100 CONTINUE                                                  GRMMT054
      RETURN                                                    GRMMT068
      END                                                       GRMMT069
C              ***********************                          MPYRT001
C              *   SUBROUTINE MPYRT  *                          MPYRT002
C              ***********************                          MPYRT003
C                                                               MPYRT004
C     MULTIPLY TWO MATRICES, THE SECOND ONE ENTERING IN TRANSPOSED  MPYRT005
C     FORM                                                      MPYRT006
C                                                               MPYRT007
C     CALL MPYRT (A,B,C,MA,NA,MSA,MB)                           MPYRT008
C                                                               MPYRT009
C         A .......... INPUT MATRIX, MA BY NA, FIRST FACTOR IN MULTI-  MPYRT010
C                      PLICATION                                MPYRT011
C         B .......... INPUT MATRIX, MB BY NA, TRANSPOSED SECOND FACTOR  MPYRT012
C                      IN MULTIPLICATION, GENERAL RECTANGULAR (MSB=0)  MPYRT013
C         C .......... OUTPUT MATRIX, MA BY MB, RESULT OF MULTIPLI-  MPYRT014
C                      CATION                                   MPYRT015
C         MA ......... NUMBER OF ROWS IN A                      MPYRT016
C         NA ......... NUMBER OF COLUMNS IN A, EQUAL TO NUMBER OF  MPYRT017
C                      COLUMNS IN B                             MPYRT018
C         MSA ........ STORAGE MODE OF A                        MPYRT019
C         MB ......... NUMBER OF ROWS IN B                      MPYRT020
C                                                               MPYRT021
```

```
      SUBROUTINE MPYRT(A,B,C,MA,NA,MSA,MB)
      DOUBLE PRECISION A,B,C,X
      DIMENSION A(1),B(1),C(1)
      MMA=MSA+1
      K=0
      ICA=0
      ICCA=0
      DO 100 J=1,MB
      INB=J
      JNB=INB
      DO 100 I=1,MA
      GOTO(12,18,17,18,16),MMA
   12 INA=I
      INCA=MA
      LLA=1
      LHA=NA
      GOTO 21
   17 INA=I
      INCA=0
      LLA=I
      LHA=I
      GOTO 21
   18 INA=I*(I-1)/2+1
      INCA=1
      LLA=1
      IF(MSA-1)73,74,73
   73 LHA=I
      GOTO 21
   74 LHA=NA
      ICCA=0
      ICA=0
      GOTO 21
   16 INA=I*(I+1)/2
      INCA=I
      ICCA=1
      ICA=0
      LLA=I
      LHA=NA
   21 K=K+1
      X=0.0D0
      IF(LLA-1)100,41,26
   26 INB=INB+(LLA-1)*MB
   41 IF(NA-LHA)100,27,27
   27 DO 30 M=LLA,LHA
      X=X+A(INA)*B(INB)
      IF(MSA-1)60,61,60
   61 IF(M-I)60,62,60
   62 INCA=I
      ICCA=1
   60 INA=INA+INCA+ICA
      ICA=ICA+ICCA
   30 INB=INB+MB
      INB=JNB
  100 C(K)=X
      CONTINUE
      IF(LTEST-1)6666,6667,6666
 6667 CONTINUE
C     CALL DPRNT(C,MA,MB,0,    6HMPYRT )
 6666 RETURN
      END
```

```
$LARGE
$D066
$NOFLOATCALLS
$NOTSTRICT
$STORAGE:2
C                                                                       INVS000
C                      **********************                           INVS001
C                      *   SUBROUTINE  INVS  *                           INVS002
C                      **********************                           INVS003
C                                                                       INVS004
C         INVERT A SYMMETRIC MATRIX (MS=1) IN PLACE AND CALCULATE THE    INVS005
C         DETERMINANT                                                   INVS006
C                                                                       INVS007
C         CALL INVS (A,N,DET,W)                                          INVS008
C                                                                       INVS009
C         A .......... INPUT-OUTPUT MATRIX, N BY N,SYMMETRIC (MS=1)      INVS010
C         N .......... NUMBER OF ROWS IN A, EQUAL TO NUMBER OF COLUMNS   INVS011
C         DET ........ OUTPUT SCALAR, DETERMINANT OF A                   INVS012
C         W .......... WORKING VECTOR OF LENGTH N                        INVS013
C                                                                       INVS014
      SUBROUTINE INVS(A,N,C,W)                                          INVS015
      DOUBLE PRECISION U,X,Y,Z,D,A,C,W                                  INVS016
       DIMENSION A(1), W(1)                                             INVS017
      INTEGER DIAGMK                                                    INVS018
      INTEGER DIAG,DIAG2,ROWNO,ROWCOL                                   INVS019
      INTEGER COLNO                                                     INVS020
      D=A(1)                                                            INVS021
      IF(D) 10,20,10                                                    INVS022
   10 A(1)=1.0D0/D                                                      INVS023
      IF(N-1)  20,20,200                                                INVS024
  200 DIAG=1                                                            INVS025
      DO 140 K=2,N                                                      INVS026
      KM1=K-1                                                           INVS027
      DIAGMK=DIAG                                                       INVS028
      DIAG=DIAG+K                                                       INVS029
      U=A(DIAG)                                                         INVS030
      COLNO=DIAGMK                                                      INVS031
      DIAG2=0                                                           INVS032
      DO 90 I=1,KM1                                                     INVS033
      X=0.0D0                                                           INVS034
      COLNO=COLNO+1                                                     INVS035
      ROWNO=DIAGMK                                                      INVS036
      J=1                                                               INVS037
      ROWCOL=DIAG2                                                      INVS038
  300 IF(J-I)  310,320,320                                              INVS039
  310 ROWCOL=ROWCOL+1                                                   INVS040
      ROWNO=ROWNO+1                                                     INVS041
      Y=A(ROWCOL)                                                       INVS042
      Z=A(ROWNO)                                                        INVS043
      X=X+Y*Z                                                           INVS044
      J=J+1                                                             INVS045
      GO TO 300                                                         INVS046
  320 ROWCOL=ROWCOL+1                                                   INVS047
   60 ROWNO=ROWNO+1                                                     INVS048
      Y=A(ROWCOL)                                                       INVS049
      Z=A(ROWNO)                                                        INVS050
      X=X+Y*Z                                                           INVS051
      ROWCOL=ROWCOL+J                                                   INVS052
      J=J+1                                                             INVS053
      IF(J-K) 60,70,70                                                  INVS054
```

```
   70 W(I)=-X                                              INVS055
      Y=A(COLNO)                                           INVS056
      U = U-X*Y                                            INVS057
      DIAG2=DIAG2+I                                        INVS058
   90 CONTINUE                                             INVS059
      D=D*U                                                INVS060
      IF(U) 100,20,100                                     INVS061
  100 A(DIAG)=1.0D0/U                                      INVS062
      ROWNO=DIAGMK                                         INVS063
      DIAG2=0                                              INVS064
      DO 140 I=1,KM1                                       INVS065
      ROWNO=ROWNO+1                                        INVS066
      DIAG2=DIAG2+I                                        INVS067
      X=W(I)                                               INVS068
      X=X/U                                                INVS069
      A(ROWNO)=X                                           INVS070
      ROWCOL=DIAG2                                         INVS071
      DO 140 J=I,KM1                                       INVS072
      Y=W(J)                                               INVS073
      Z=A(ROWCOL)                                          INVS074
      A(ROWCOL)=Z+X*Y                                      INVS075
      ROWCOL=ROWCOL+J                                      INVS076
  140 CONTINUE                                             INVS077
   20 C=0                                                  INVS078
      IF(C)6665,99,6665                                    INVS079
   99 WRITE(*,97)                                          INVS080
   97 FORMAT(' ERROR MESSAGE FROM SUBROUTINE INVS ......... MATRIX IS SI INVS081
     1NGULAR'/'1')                                         INVS082
      CONTINUE                                             INVS083
 6665 CONTINUE                                             INVS084
      IF(LTEST-1)6666,6667,6666                            INVS085
 6667 CONTINUE                                             INVS086
C     CALL DPRNT(A,N,N,1,6HINVS  )                         INVS087
 6666 RETURN                                               INVS088
      END                                                  INVS089
C                                                          SCM000
C                                                          SCM001
C              ************************                    SCM001
C              *   SUBROUTINE   SCM   *                    SCM002
C              ************************                    SCM003
C                                                          SCM004
C        MULTIPLY A MATRIX BY A SCALAR                     SCM005
C                                                          SCM006
C        CALL SCM (A,X,B,M,N,MS)                           SCM007
C                                                          SCM008
C        A .......... INPUT MATRIX, M BY N                 SCM009
C        X .......... SCALAR CONSTANT OR VARIABLE, FACTOR IN MULTI-  SCM010
C                     PLICATION                            SCM011
C        B .......... OUTPUT MATRIX, M BY N, RESULT OF MULTIPLICATION SCM012
C        M .......... NUMBER OF ROWS IN A                  SCM013
C        N .......... NUMBER OF COLUMNS IN A               SCM014
C        MS ......... STORAGE MODE OF A                    SCM015
C                                                          SCM016
      SUBROUTINE SCM(A,C,B,M,N,MS)                         SCM017
      DOUBLE PRECISION A,B,C                               SCM018
      DIMENSION A(1),B(1)                                  SCM019
      MMS=MS+1                                             SCM020
      GOTO(99,199,299,199,199),MMS                         SCM021
   99 MN=M*N                                               SCM022
      GO TO 499                                            SCM023
  199 MN=(M*(M+1))/2                                       SCM024
```

```
      GO TO 499                                                   SCM025
  299 MN=M                                                        SCM026
  499 DO 500 I=1,MN                                               SCM027
  500 B(I)=C*A(I)                                                 SCM028
      CONTINUE                                                    SCM029
      IF(LTEST-1)6666,6667,6666                                   SCM030
 6667 CONTINUE                                                    SCM031
C     CALL DPRNT(B,M,N,MS,       6HSCM   )                        SCM032
 6666 RETURN                                                      SCM033
      END                                                         SCM034
C                                                                 CHAMS000
C                                                                 CHAMS001
C                    **********************                       CHAMS001
C                    *  SUBROUTINE CHAMS  *                       CHAMS002
C                    **********************                       CHAMS003
C                                                                 CHAMS004
C        CHANGE MODE OF STORAGE OF A SQUARE MATRIX FROM ONE PACKED FORMCHAMS005
C        TO ANOTHER                                               CHAMS006
C                                                                 CHAMS007
C        CALL CHAMS (A,B,N,MSA,MSB)                               CHAMS008
C                                                                 CHAMS009
C        A ......... INPUT MATRIX, N BY N                         CHAMS010
C        B ......... OUTPUT MATRIX, N BY N                        CHAMS011
C        N ......... NUMBER OF ROWS IN A, EQUAL TO NUMBER OF COLUMNS CHAMS012
C        MSA ....... STORAGE MODE OF A                            CHAMS013
C        MSB ....... DESIRED STORAGE MODE OF B, UNEQUAL TO MSA    CHAMS014
C                                                                 CHAMS015
      SUBROUTINE CHAMS(A,B,N,MSA,MSB)                             CHAMS016
      DOUBLE PRECISION A,B                                        CHAMS017
      DIMENSION A(N,1),B(N,1)                                     CHAMS018
      MMS=5*MSA+MSB+1                                             CHAMS019
      GOTO(99,11,12,20,11,13,99,14,99,99,13,16,99,16,16,50,99,14,99,99,5CHAMS020
     10,99,14,99,99),MMS                                          CHAMS021
   99 WRITE(*,98)                                                 CHAMS022
   98 FORMAT(' ERROR MESSAGE FROM SUBROUTINE CHAMS .......... ILLICIT COCHAMS023
     1MBINATION OF STORAGE MODES'/'1')                            CHAMS024
      CONTINUE                                                    CHAMS025
C     SQUARE TO SYMMETRIC                                         CHAMS026
   11 K = 0                                                       CHAMS027
      DO 3 J=1,N                                                  CHAMS028
      DO 3 I=1,J                                                  CHAMS029
      K = K + 1                                                   CHAMS030
    3 B(K,1) = A(I,J)                                             CHAMS031
      GO TO 6665                                                  CHAMS032
C     SQUARE TO DIAGONAL                                          CHAMS033
   12 DO 111 J=1,N                                                CHAMS034
  111 B(J,1) = A(J,J)                                             CHAMS035
      GO TO 6665                                                  CHAMS036
C     TRANSPOSITION FOR LOWER TRIANGLES                           CHAMS037
   20 DO 1 J=2,N                                                  CHAMS038
      L=J-1                                                       CHAMS039
      DO 1 I=1,L                                                  CHAMS040
      IF(MSA.EQ.3)GOTO115                                         CHAMS041
      A(I,J)=A(J,I)                                               CHAMS042
      A(J,I)=0.0D0                                                CHAMS043
      GOTO1                                                       CHAMS044
  115 B(J,I)=B(I,J)                                               CHAMS045
      B(I,J)=0.0D0                                                CHAMS046
    1 CONTINUE                                                    CHAMS047
      IF(MSA-3)11,6665,99                                         CHAMS048
C     SYMMETRIC TO SQUARE                                         CHAMS049
```

```
   13 L = N + 1
      K = (N*L)/2 + 1
      DO 212 J=1,N
      JR = L - J
      DO 212 I=1,JR
      IR = JR + 1 - I
      K = K - 1
  212 B(IR,JR) = A(K,1)
      DO 121 J=2,N
      DO 121 I=1,J
  121 B(J,I) = B(I,J)
      GO TO 6665
C     DIAGONAL TO SQUARE
   15 DO 213 J=2,N
      DO 213 I=1,N
  213 B(I,J) = 0.0D0
      DO 222 J=1,N
  222 B(J,J) = A(J,1)
      DO 131 J=2,N
  131 B(J,1) = 0.0D0
      GO TO 6665
C     SYMMETRIC TO DIAGONAL
   14 I = 0
      DO 414 J=1,N
      I = I + J
  414 B(J,1) = A(I,1)
      GO TO 6665
C     DIAGONAL TO SYMMETRIC
   16 L = N + 1
      LN = L
      K = (N*L)/2
      DO 415 J=1,N
      M = LN - J
      L = L - 1
      B(K,1) = A(L,1)
  415 K = K - M
      L = 2
      DO 525 J=2,N
      LL = L + J - 2
      DO 232 I=L,LL
  232 B(I,1) = 0.0D0
  525 L = L + J
      GO TO 6665
C     UPPER TRUE TRIANGLE TO SQUARE
   50 L = N + 1
      K = (L*N)/2 + 1
      DO 515 J=1,N
      JR = L - J
      DO 515 I=1,JR
      IR = JR + 1 - I
      K = K - 1
  515 B(IR,JR) = A(K,1)
      DO 535 J=2,N
      L = J - 1
      DO 535 I=1,L
  535 B(J,I) = 0.0D0
      IF(MSA.EQ.3)GOTO20
 6665 CONTINUE
      IF(LTEST-1)6666,6667,6666
 6667 CONTINUE
```

```
C      CALL DPRNT(B,N,N,MSB,6HCHAMS )                              CHAMS110
6666   RETURN                                                      CHAMS111
       END                                                         CHAMS112
C                                                                  DPRNT000
C                    ***********************                       DPRNT001
C                    *   SUBROUTINE DPRNT  *                       DPRNT002
C                    ***********************                       DPRNT003
C                                                                  DPRNT004
C          DIAGNOSTIC PRINT-OUT OF RESULTS                         DPRNT005
C                                                                  DPRNT006
C          CALLED BY INDIVIDUAL SUBROUTINES IF SENSE LIGHT 4 IS ON DPRNT007
C                                                                  DPRNT008
       SUBROUTINE DPRNT(C,M,N,MS,SUBNAM)                           DPRNT009
       IMPLICIT REAL*8(A-H,O-Z)                                    DPRNT010
         CHARACTER*8 SUBNAM,ROW
         CHARACTER*4 HEAD,TITLE,S,SS
       DIMENSION TITLE(15),S(2),C(1),HEAD(30)                      DPRNT012
       EQUIVALENCE (S(1),SS)                                       DPRNT013
       DATA ROW/'      '/                                          DPRNT014
       DATA HEAD /'    ',' ',' ',' ',' ',' ',' ',' ','DPRNT015
      *,'    ',' ',' ',' ',' ',' ',' ',' ',' ',' ',' ',' DPRNT016
      *   ',' ',' ',' ',' ',' ',' ',' ',' ',' ',' ',     DPRNT017
      *',' ',' ',' '/                                              DPRNT018
       DATA TITLE/'    ',' DIA','GNOS','TIC ','PRIN','T-OU','T FR','OM S'DPRNT019
      * ,'UBRO','UTIN','E  ..','.....','.....',' ',' ','/          DPRNT020
       SS=SUBNAM                                                   DPRNT021
       TITLE(14)=S(1)                                              DPRNT022
       TITLE(15)=S(2)                                              DPRNT023
       NP=-1                                                       DPRNT024

C      CALL PRINT(C,M,N,MS,ROW,ROW,NP,HEAD,TITLE)                  DPRNT025
       RETURN                                                      DPRNT026
       END                                                         DPRNT027
```

As will be apparent to those of skill in the art, the above program is a Fortran language source code which may be readily utilized with any suitable computing device such as an IBM AT personal computer in the preferred embodiment. The customized sub-routines utilized in the main program are defined following the program. A number of sub-routines are called but not defined in the readout. Each of these sub-routines is available in a fixed format from the Halo Fortran Library for use with a Microsoft Fortran 3.2 compiler. Specifically, the sub-routines INITGR, CLOSEG, MOVTCA, TEXT, DELCTU, PRINT, MOVABS, LNABS, and BOX may be readily obtained from that library. Alternatively, other suitable stock sub-routines may be substitutes for these. These sub-routines deal with the input and output of information and formatting of the display; none concern the actual calculations of the appropriateness of the estimated fit. Accordingly, they may be replaced with others which may be more suitable for any desired display format, depending upon the particular application of the the present invention as determined by the user.

In the calculations performed in the preferred embodiment of the present invention, a common standard deviation is assumed for each of the component distributions in the multiple-component field being analyzed. Such an assumption should normally provide acceptable data and successfully avoid a nondeterminative situation which is possible when a calculation of separate standard deviations is required. Further, it has empirically been determined that the means and method of the present invention will most accurately identify the relative proportional content of each component in the selected multiple-component field when the difference between the mean value for each component is on the order of approximately two standard deviation units.

Although it is generally desirable to maintain the field analysis conditions in an unaltered state for successive measurements of the proportional content for any selected field to obtain an accurate measure of the relative changes in proportional content, it is not necessary in all instances. For example, the lighting used to illuminate the selected field may vary greatly because the means and method of the present invention operate in a generally scaleless fashion. The accumulation of the gray value data, as shown by histograms such as in FIG. 5 about readily identifiable mean locations, allows the calculations to provide the desired results. Accordingly, the exact mean gray value for each component is generally unimportant. If for example, in analyzing human head region 12, the lighting from lights 13 and 23 is made significantly brighter during a subsequent analysis, the gray values indicated on FIG. 5 will be merely shifted to the right, indicating more light in the photograph. However, the separation between the mean values representative of hair and scalp, respectively, should remain approximately the same. Similarly, in conjunction with the example illustrated in FIGS. 1 and 2, a change in hairstyle of the subject may not distort the data, as long as it is not too severe. Tests have shown that a one-half (½) inch haircut between a first observation and an immediately succeeding second observation resulted in a negligible percentage change in the measured hair density in the head region 12.

However, the positioning of the camera has been determined to be a relatively important factor. When the distance between the subject, i.e., selected field area, and the camera is altered too greatly, a significant change in the measured proportional content may occur. Accordingly, it is suggested that the camera distance be maintained approximately constant for successive measurements in order to obtain an accurate measure of any change in the proportional content for each component.

Another factor which may adversely impact on the accuracy of the means and method of the present invention is the degree of distinctiveness between the various components which comprise the field to be analyzed. This phenomenon may occur because of the lack of separation between the component peaks in the digitized gray level data, such as is shown in FIG. 5. As mentioned above, the separation between the mean gray level values for hair and scalp in FIG. 5 is on the order of two standard deviation units. The data for FIG. 5 was generated from a Caucasian male with dark hair. However, when the separation between the mean gray-level values falls to less than two standard deviation units, as may occur when a blond, fair-skinned or a dark-haired, dark-skinned individual is to be tested, the technique of the preferred embodiment may provide less conclusive results.

For such occasions, alternative methods for obtaining distinct and identifiable peaks in the measured data may be desirable. For example, infrared analysis might provide the requisite distinctiveness between the recorded gray levels of the components, when a simple visible light analysis proves inconclusive.

Also, the field need not be recorded in black and white to allow the successful practice of the present invention. Color field representations may be likewise digitized and resolved into identifiable, discrete gray levels.

Figure 10:
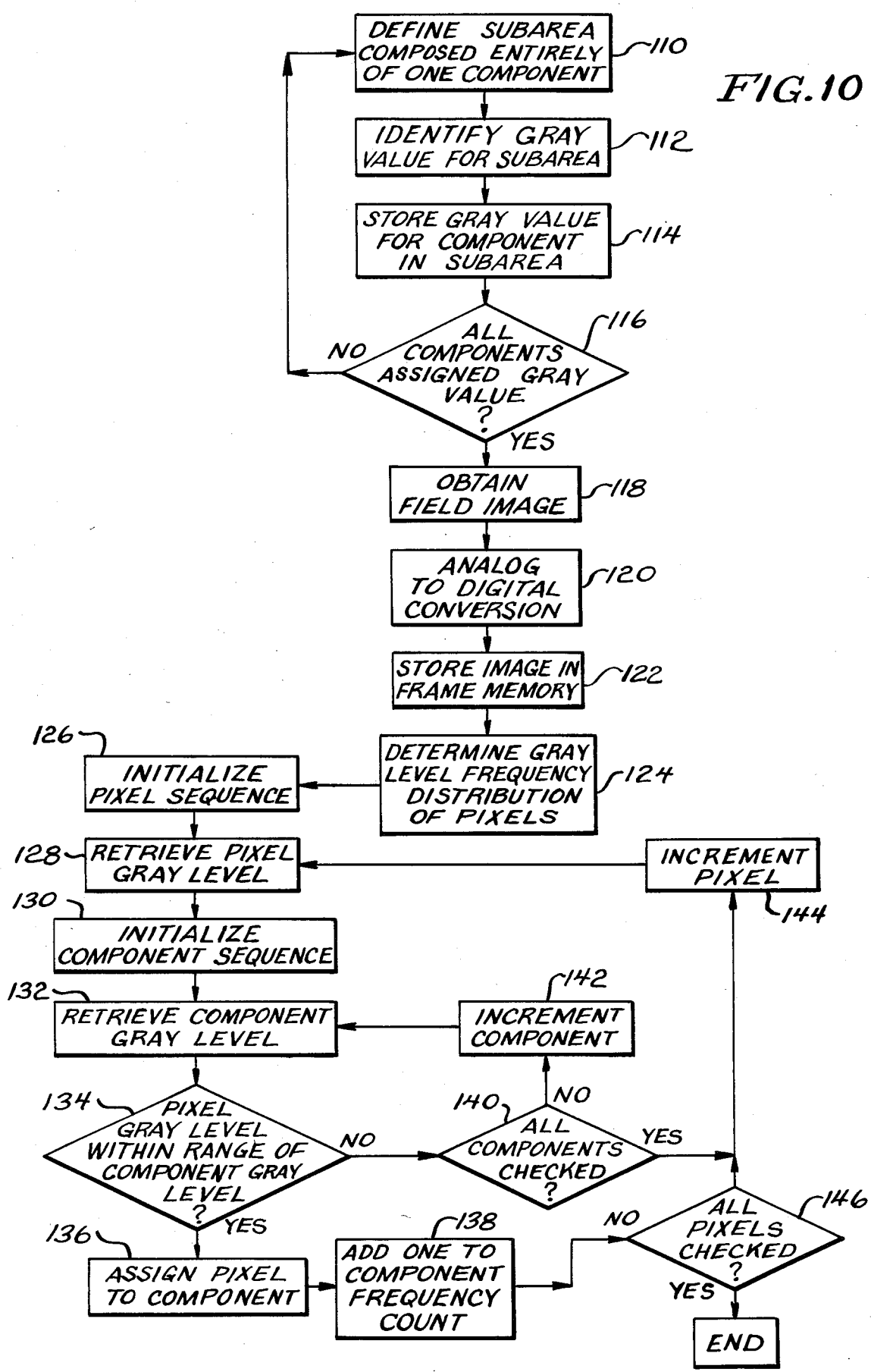
FIG. 10 is a schematic flowchart representation of an additional embodiment for digital analysis in accordance with the present invention.

In accordance with the means and method of the present invention, several alternative embodiments may be utilized to measure the relative proportional content of each component in a multiple-component field. Referring now to FIG. 10, therein is shown one such alternative embodiment. A selected sub-area of a multiple-component field in which only a single component is present is initially defined as shown by block 110. The mean gray-scale value for that component is then identified as shown by block 112 and stored in accordance with block 114. This is then repeated for all sub-areas of the field in which only a single component is present, until a mean gray-scale value for each component has been identified as shown by decision block 116. Once the gray-scale value for each component has been identified, the entire selected field area, such as that of head area 2 in FIG. 2, may be analyzed as above to provide digitized information and a histogram of the gray-scale values for each pixel in the field in accordance with blocks 118, 120, 122 and 124. The number of digitized pixels having gray-scale values falling within a predetermined range about the mean gray-scale value for each component may then be registered as shown generally by the steps of blocks 126, 128, 130, 132, 136, 138, 142 and 144 implemented by decision blocks 134, 140 and 146 and the illustrated logic loops. These measured quantities will be generally representative of the proportional content of each identified component in the entire multiple-component field.

More particularly, at block 126 the first pixel is selected, and its gray level is retrieved from storage at block 128. At block 130 the first-component is selected, and its gray level is retrieved at block 132. As per decision block 134 the first pixel gray level and the first-component gray level are compared to determine whether the pixel value falls within a predetermined or preselected range of the component value. If so, then the pixel is assigned to that component, as per block 136, and that component frequency count is increased by one, as per block 138. If the pixel value is not within the desired range, a check is made whether all of the component values have been compared to the first pixel value as per decision block 140. If not, then the component count is incremented and the comparison steps repeated until all the component values have been compared to the pixel value or the pixel value falls within the desired range and is identified as a particular component per block 136. If all of the component values have been compared to the pixel value without an assignment being made, the pixel count is incremented as per block 144. The above steps are then repeated until all of the pixels, or at least all pixel gray levels, have been analyzed as per decision block 146, at which time the analysis is complete.

Figure 11:
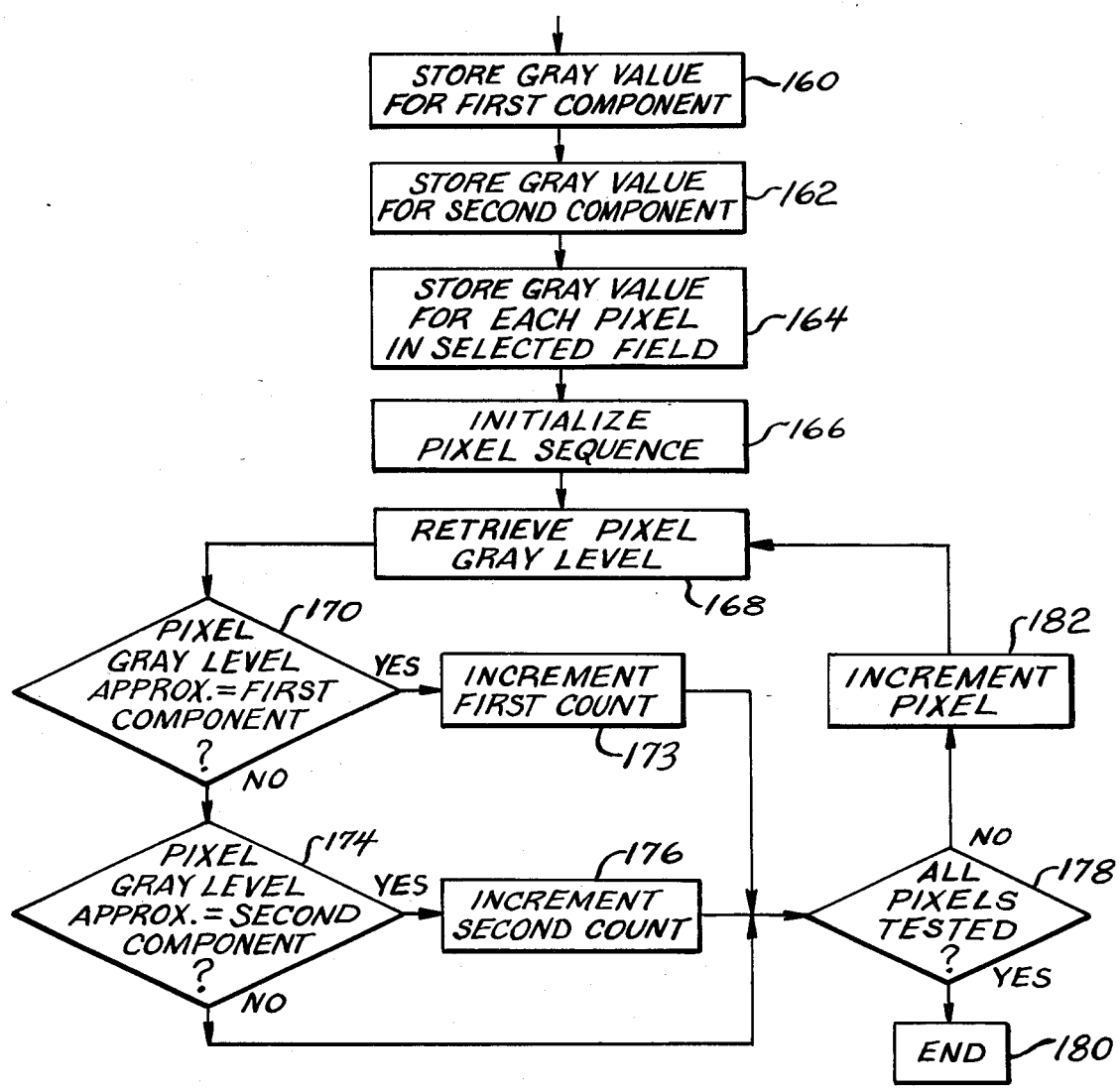
FIG. 11 is a schematic flowchart representation of an additional embodiment for digital analysis in accordance with the present invention.

A further simplified embodiment of the means and method of the present invention is illustrated generally by the flowchart of FIG. 11. When it has been previously, presumably visually, determined that the selected multiple-component field comprises only two components and these two components are readily identifiable as a lighter and darker component, the digitized information for the gray level pixels may be resolved quickly into either one or the other of the two components. In this type of analysis, an average mean gray-scale value is determined as the average of the mean for the lighter component and the mean for the darker component, which may be determined as above by recording and analyzing selected single component subregions of the field or by any other suitable method. All pixels having a gray-scale value greater than the average means would be identified as belonging to the lighter component. All pixels having a gray-scale value less than the average mean gray-scale value would be identified as comprising the darker component. Accordingly, the quantitative analysis of the number falling into either category would provide a ready approximation of the proportional content of each component in the multiple-component field.

Referring now to FIG. 11, a similar method is generally outlined. In block 160 a gray value for the first-component is identified and stored. The step of block 162 identifies and stores a gray value for the second-component. As per block 164, each pixel in the selected field is then analyzed and a gray level is stored for each.

A first pixel is then chosen as per block 166 and its gray level retrieved at block 168. Decision block 170 illustrates the first half of the test. If the pixel gray level is approximated by that of the first-component, a first count is incremented at block 172. If not, then the pixel gray level is evaluated against that of the second-component at that decision block 174. If that value approximates the pixel's, then a second count is incremented at block 176. If not, that pixel is discounted.

Subsequently, at decision block 178, a test is run to see if all pixels in the field have been evaluated. If so, then the process ends at block 180. If not, the block 182 moves the analysis to the next pixel in sequence and the process is repeated until all of the pixels have been evaluated. The proportion of the field comprised of the first-component is then given by the ratio of the first count to the sum of the two counts.

When the component mean gray values are averaged as described above, decision blocks 170 and 174 are consolidated and a greater than or less than test is run. If the pixel gray value is greater than the average of the means, then a first count is incremented; if less than, a second count is incremented, until all of the pixels are evaluated. The proportion of the field comprised of the first-component is again given by the ratio of the first count (if the first-component is lighter than the second; by the second count if the first-component is darker than the first) to the sum of the two counts.

Although described above in terms of a preferred embodiment for monitoring hair growth over a selected observation period, means and method of the present invention may be readily utilized in other environments with equal success. For example, it is envisioned that the present invention may be used to monitor the proportion of facial skin infected with acne or to the degree and extent of skin irritation, erythemia, resulting from topical application of various substances, such as a putative industrial irritant. Finally, it is envisioned that the present invention may be used to analyze virtually any multiple-component field having readily available, fairly distinct components.

What I claim is:

1. A method for digitally analyzing two component fields, comprised of human hair and human scalp, each having a relatively distinct, visible intensity, to measure a relative proportional content of each component comprising:
   recording a selected field area to create a record having a plurality of discrete segments of varying intensity;
   digitally resolving the intensity of each of said discrete segments into one of a multiple of discrete values;
   registering a frequency of occurrence of each said multiple of discrete values in said field to obtain a frequency distribution; and
   resolving said frequency distribution into multiple, normally distributed component distributions, through a Gaussian mixture analysis, each being representative of a selected component to provide a first measure of a proportional content of said field comprised of each component.

2. The method of claim 1 further including visually displaying said record of said selected field area.

3. The method of claim 1 further including displaying said frequency distribution.

4. The method of claim 3 further including tangibly recording said frequency distribution.

5. A method for digitally analyzing multiple-component fields to measure a relative proportional content of each component comprising:
   recording a selected field area to create a record having a plurality of discrete segments of varying intensity;
   digitally resolving the intensity of each of said discrete segments into one of a preselected multiple of discrete values;
   registering a frequency of occurrence of each said preselected multiple of discrete values in said field to obtain a frequency distribution;
   resolving said frequency distribution into multiple, normally distributed component distributions, through a Gaussian mixture analysis, each being representative of a selected component to provide a first measure of a proportional content of said field comprised of each component;
   storing a log likelihood for a single Gaussian distribution of said frequency distribution;
   storing a log likelihood for a two component, mixed Gaussian distribution of said frequency distribution; and
   comparing said stored values to obtain a difference between said stored values, whereby said field may be approximated by a two-component Gaussian mixture distribution if said stored values differ by a predetermined amount.

6. A method for digitally analyzing multiple-component fields to measure a relative proportional content of each component comprising:
   recording a selected field area to create a record having a plurality of discrete segments of varying intensity;
   digitally resolving the intensity of each of said discrete segments into one of a preselected multiple of discrete values;
   registering a frequency of occurrence of each said preselected multiple of discrete values in said field to obtain a frequency distribution;
   resolving said frequency distribution into multiple, normally distributed component distributions, through a Gaussian mixture analysis, each being representative of a selected component to provide a first measure of a proportional content of said field comprised of each component;
   storing a log likelihood for a single Gaussian distribution of said frequency distribution;
   storing a log likelihood for a two component, mixed Gaussian distribution of said frequency distribution; and
   comparing said stored values to obtain a difference between said stored values, whereby said field may be approximated by a two-component Gaussian mixture distribution if said stored values differ by a predetermined amount.
   repeating each step after a selected observation period to provide a second measure of the proportional content of said field comprised of each component; and
   comparing said second proportional content measure with the first proportional content measure to register any change in the proportional content of each component.

7. A method of monitoring a relative proportional content of each component in a multiple-component visible field comprising:
   recording a selected visible field to create a first record of said selected visible field, said record having a plurality of discrete portions of varying visible intensity;
   digitally resolving the visible intensity of each of said discrete portions into one of a preselected multiple of discrete values;
   determining a frequency of occurrence of each discrete value in said visible field to obtain a frequency distribution;

resolving said frequency distribution through a Gaussian mixture analysis into a plurality of multiple, normally distributed component distributions, each of said component distributions being representative of a selected component in said visible field, thereby providing a first proportional measure of said visible field comprised of each component;

repeating the above steps after a selected interval to create a second record of said preselected visible field to obtain a second set of multiple, normally distributed component distributions to provide a second proportional measure of the field comprised of each component; and comparing said second proportional measure with said first proportional measure to register any change in the relative proportional content of each component in said selected visible field.

8. A method for digitally analyzing multiple-component visible fields to determine a relative proportional content of each component comprising:

A. recording a first section of a selected visible field area to create a record of said first section, said first section being comprised substantially of a first-component having a first visible intensity;

B. digitally resolving the visible intensity of said first-component into a first of a preselected multiple of discrete values;

C. repeating the above steps to identify discrete digital values for the visible intensity of each component in said multiple-component visible field;

D. recording said visible field area to create a record of said selected visible field area, said record having a plurality of discrete segments of varying visible intensity;

E. digitally resolving the visible intensity of each of said discrete segments into one of said preselected multiple of discrete values;

F. registering a frequency of occurrence of discrete segment values within a predetermined range of each of said digital component values, whereby a proportional measure of a content of said visible field comprised of each component is provided by a proportion of said plurality of discrete segments having discrete values within said range of each component.

9. The method of claim 8 further including:

repeating steps D, E and F after a selected interval to provide a second proportional measure of the content of said visible field comprised of each component;

comparing said second proportional measure with said first proportional measure to register any change in the proportional content of each component in said selected visible field.

10. A method for digitally analyzing a human scalp region to measure a proportion of scalp area comprised of hair relative to that area comprised of bare skin comprising the steps of:

recording said scalp region to create a record of said scalp region, said record having a plurality of discrete segments of varying visible intensity;

digitally resolving the visible intensity of each of said discrete segments into one of a preselected multiple of discrete values;

storing a count of each said discrete value in said scalp region to obtain a frequency distribution;

resolving said frequency distribution through a Gaussian mixture analysis into two normally distributed component Gaussian distributions, one of said component distributions being representative of the visible intensity of hair and the other component distribution being representative of the visible intensity of bare skin, thereby providing a measure of a relative proportional content of hair in the scalp region.

11. Apparatus for visually analyzing multiple-component fields to determine a relative proportional content of each component comprising:

means for recording a selected field to create a record having a plurality of discrete segments of varying intensity;

means for digitally resolving the intensity of each of said discrete segments of said record from said means for recording into one of a multiple of discrete values;

means for registering a frequency of occurrence of each discrete value resolved by said means for digitally resolving in said field to obtain a frequency distribution;

means for resolving said frequency distribution from said means for registering digital resolution means for resolving said frequency distribution through a Gaussian mixture analysis into multiple, normally distributed component distributions, each being representative of a component in said fields for measuring the proportional content of said field composed of each component.

12. The apparatus of claim 11 wherein said means for recording comprises visual recording means.

13. The apparatus of claim 12 wherein said visual recording means comprises a video camera.

14. The apparatus of claim 11 wherein said means for resolving comprises a digital computer.

15. The apparatus of claim 11 wherein said means for digitally resolving comprises digitizer circuitry.

* * * * *